(12) United States Patent
Morgenroth et al.

(10) Patent No.: US 11,305,289 B2
(45) Date of Patent: Apr. 19, 2022

(54) METHOD FOR AUTOMATED DETECTION OF ANTIBODIES IN A LIQUID BIOLOGICAL SAMPLE USING AN ANTIGEN CHIP, AND ANTIGEN CHIP THEREFOR

(71) Applicant: EUROIMMUN Medizinische Labordiagnostika AG, Luebeck (DE)

(72) Inventors: Katja Morgenroth, Herrnburg (DE); Vanessa Viertel, Luebeck (DE); Ulf Steller, Buchholz (DE); Stefan Gerlach, Gross Groenau (DE); Christian Marzahl, Erlangen (DE); Jörn Voigt, Luebeck (DE); Winfried Stöcker, Gross Groenau (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 0 days.

(21) Appl. No.: 17/250,216

(22) PCT Filed: Jun. 17, 2019

(86) PCT No.: PCT/EP2019/065874
§ 371 (c)(1),
(2) Date: Dec. 16, 2020

(87) PCT Pub. No.: WO2020/007597
PCT Pub. Date: Jan. 9, 2020

(65) Prior Publication Data
US 2021/0245152 A1    Aug. 12, 2021

(30) Foreign Application Priority Data
Jul. 6, 2018  (EP) ........................................ 8182266

(51) Int. Cl.
*G01N 21/64* (2006.01)
*B01L 3/00* (2006.01)
(Continued)

(52) U.S. Cl.
CPC ...... *B01L 3/50855* (2013.01); *G01N 21/6428* (2013.01); *G01N 21/6447* (2013.01);
(Continued)

(58) Field of Classification Search
CPC .... B01L 3/50855; B01L 3/5085; B01L 3/508; B01L 3/50; G01N 21/6428; G01N 21/64
(Continued)

(56) References Cited

U.S. PATENT DOCUMENTS 9,566,560 B2    2/2017  Harris et al.
2005/0135964 A1  6/2005  Sieben
(Continued)

FOREIGN PATENT DOCUMENTS

DE  10 2006 027 517   12/2007
DE  10 2008 060 991    6/2010
(Continued)

OTHER PUBLICATIONS

International Search Report dated Jul. 23, 2019 in PCT/EP2019/065874 with English translation, 5 pages.
(Continued)

*Primary Examiner* — Christine T Mui
(74) *Attorney, Agent, or Firm* — Grüneberg and Myers PLLC

(57) ABSTRACT

A method is useful for automated detection of antibodies in a liquid biological sample with an antigen chip having antigen spots which are applied thereon and which have an identical, common dye. The antigen spots form respective antigen spot sets which form corresponding respective, regular antigen spot patterns. Furthermore, reference spots comprising the identical dye are applied, and form a reference spot set which forms a regular reference pattern. The reference pattern differs with respect to its regularity from the antigen spot patterns. Through a first image information
(Continued)

item which represents a color of the reference spots and of the antigen spots due to the identical, first dye and through a second image information item which represents a potential color of the antigen spots due to a second dye after an incubation, binding of antibodies of the biological sample to respective antigen types is then determined by image processing.

21 Claims, 18 Drawing Sheets

(51) Int. Cl.
*G01N 33/58* (2006.01)
*G01N 33/543* (2006.01)

(52) U.S. Cl.
CPC ........... *G01N 33/543* (2013.01); *G01N 33/58* (2013.01); *G01N 2021/6439* (2013.01)

(58) Field of Classification Search
USPC ................... 422/552, 500; 436/172; 435/7.1
See application file for complete search history.

(56) References Cited

U.S. PATENT DOCUMENTS

| | | | |
|---|---|---|---|
| 2010/0284859 A1* | 11/2010 | Cooney | B01J 19/0046 422/68.1 |
| 2011/0275539 A1 | 11/2011 | Spatz et al. | |
| 2017/0016052 A1 | 1/2017 | Cooney et al. | |

FOREIGN PATENT DOCUMENTS

| | | |
|---|---|---|
| EP | 2 362 222 | 8/2011 |
| JP | 2003322651 | 11/2003 |
| JP | 201350719 | 3/2013 |
| JP | 2013508732 | 3/2013 |
| JP | 2016527918 | 9/2016 |
| WO | 2012/142397 | 10/2012 |

OTHER PUBLICATIONS

Written Opinion dated Jul. 23, 2019 in PCT/EP2019/065874 with English translation, 10 pages.
European Search Report dated Nov. 28, 2018 in European Application No. 18182266.9 with partial English translation, 8 pages.
EPO Article 94 (3) Communication dated Aug. 2, 2019 in European Application No. 18182266.9 with partial English translation, 6 pages.
European Search Report dated Nov. 2, 2018 in European Application No. 18182267.7 with partial English translation, 11 pages.
EPO Rule 71 (3) Communication dated Feb. 6, 2020 in European Application No. 18182266.9 with partial English translation, 84 pages.
EPO Article 94 (3) Communication dated Aug. 27, 2020 in European Application No. 18182266.9 with partial English translation, 5 pages.
Extended European Search Report dated Jul. 23, 2019 in European Application No. 1917943.3 with partial English translation, 11 pages.
EPO Rule 71 (3) Communication dated Jul. 6, 2020 in European Application No. 19179434.6 with English translation, 52 pages.
European Search Report dated Jul. 22, 2019 in European Application No. 19180580.3 with partial English translation, 8 pages.
Anonymous, Figure 2 [Spectral overlap and FRET], Assay Guidance Manual, NCBI Bookshelf, A service of the National Library of Medicine, National Institutes of Health, Feb. 1, 2020.
Japanese Office Action dated Oct. 12, 2021in Japanese Appliation No. 2021-500209, with English translation, 9 pages.

* cited by examiner

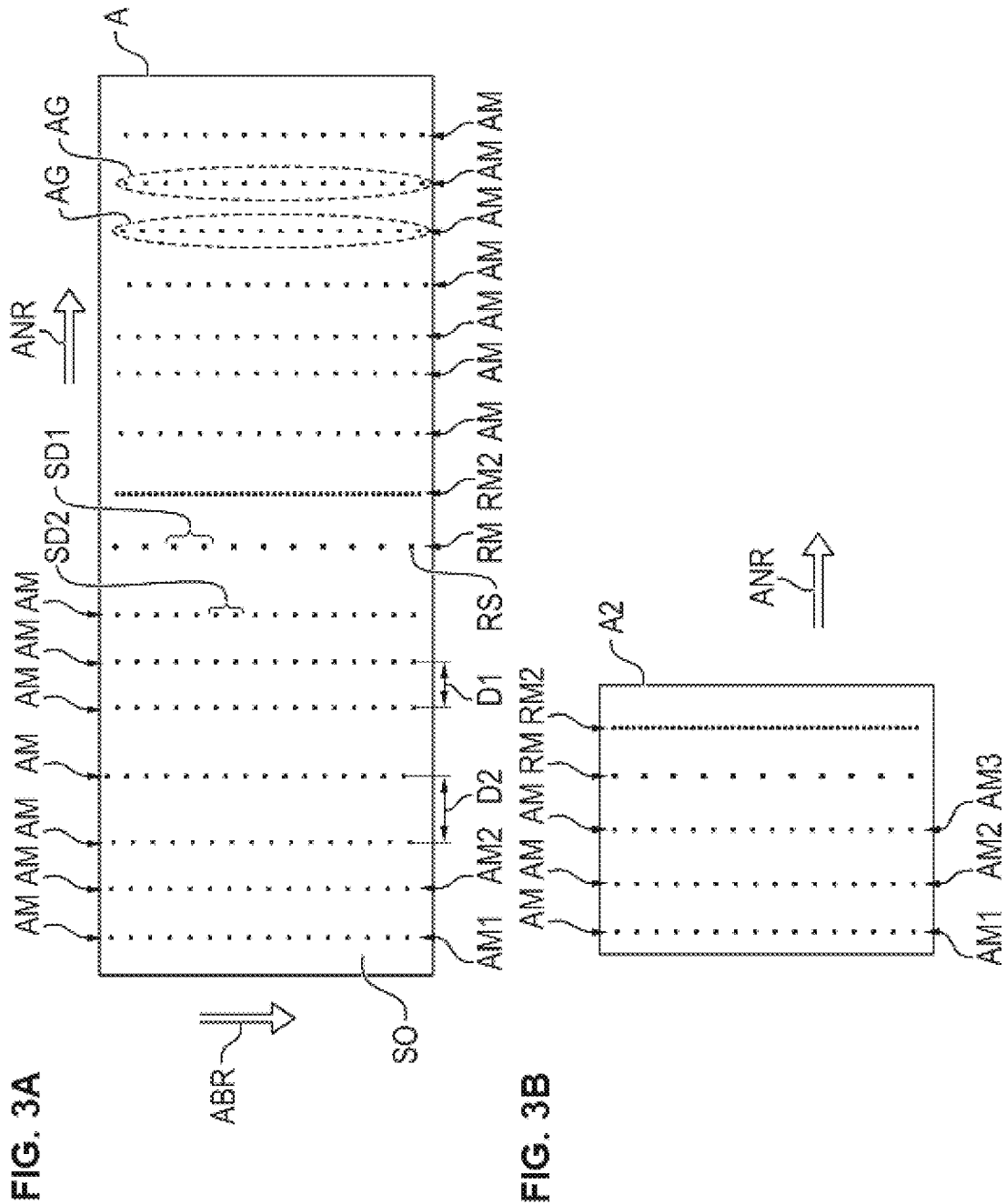

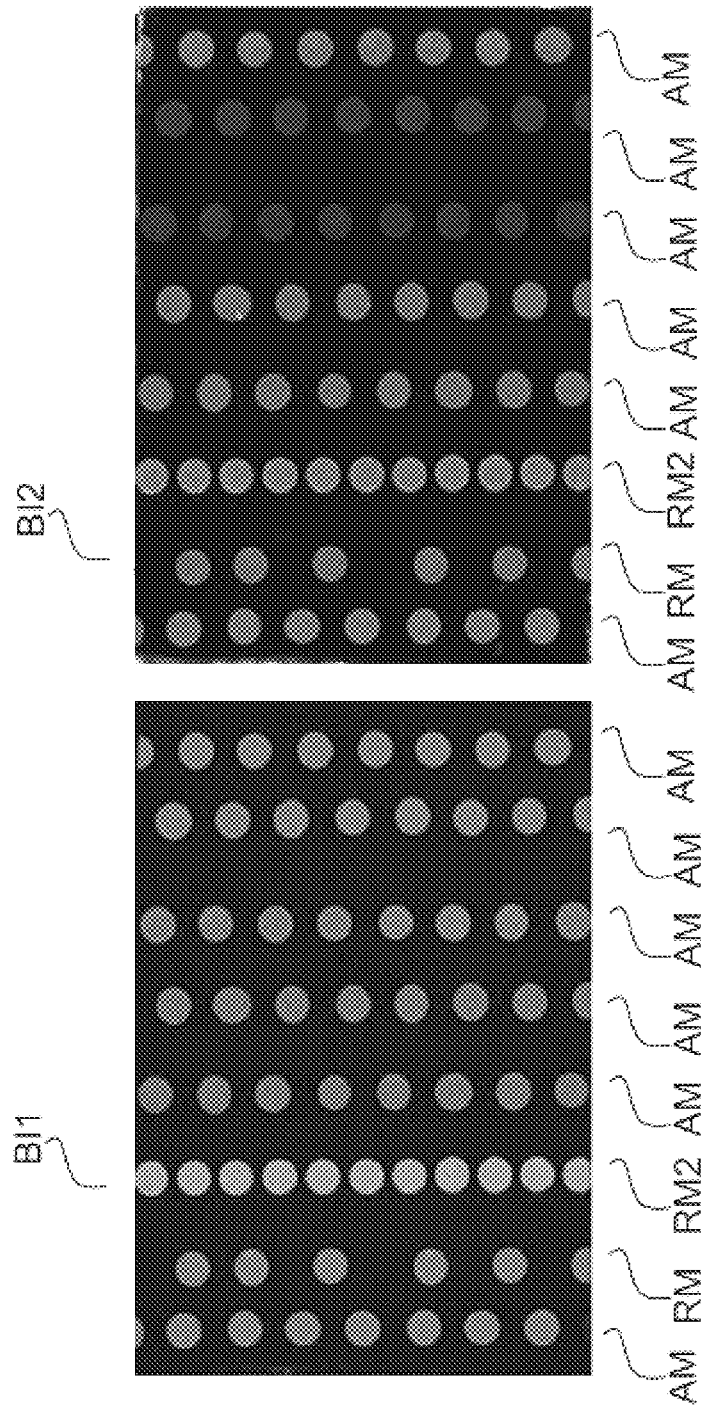

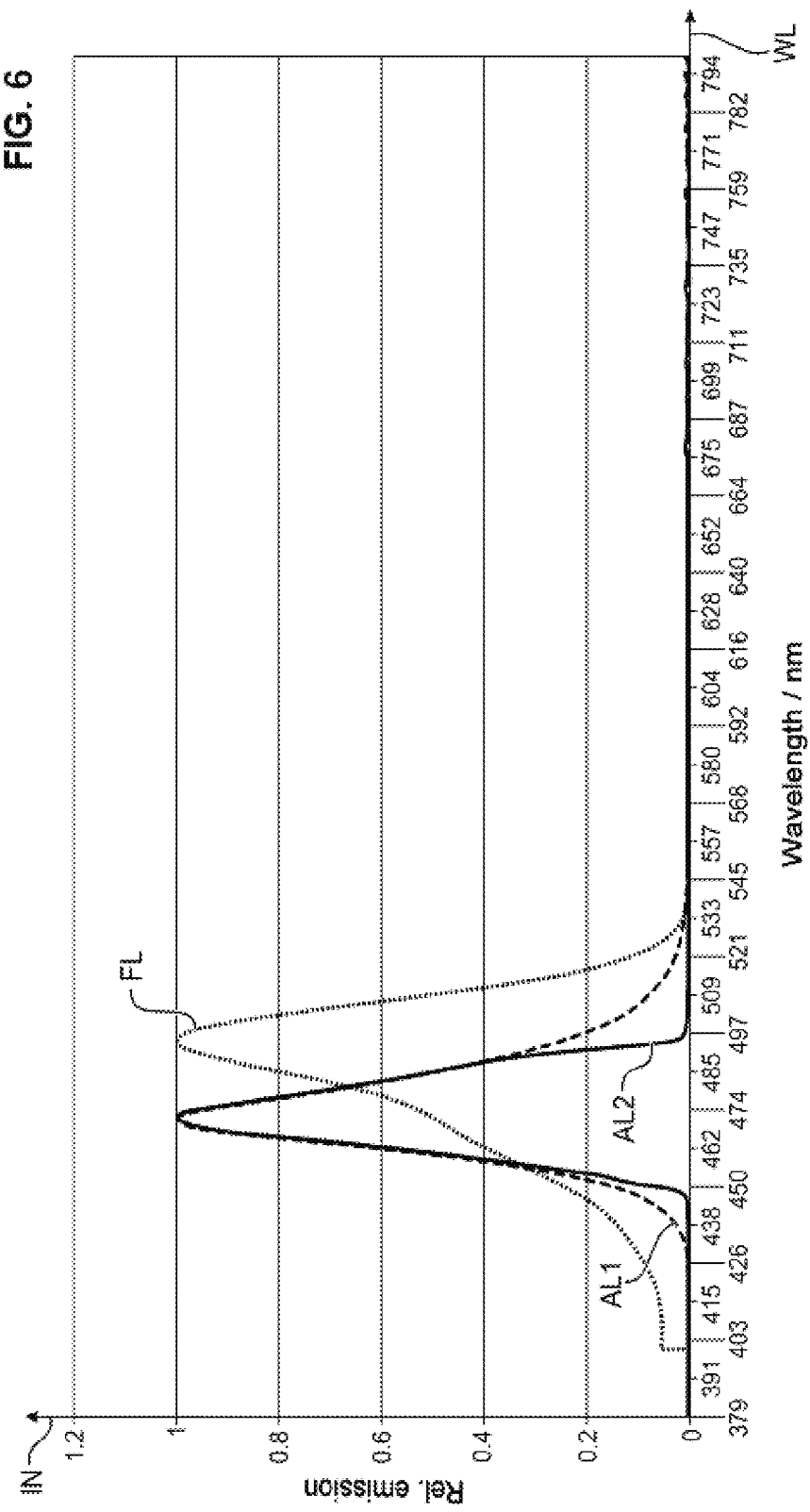

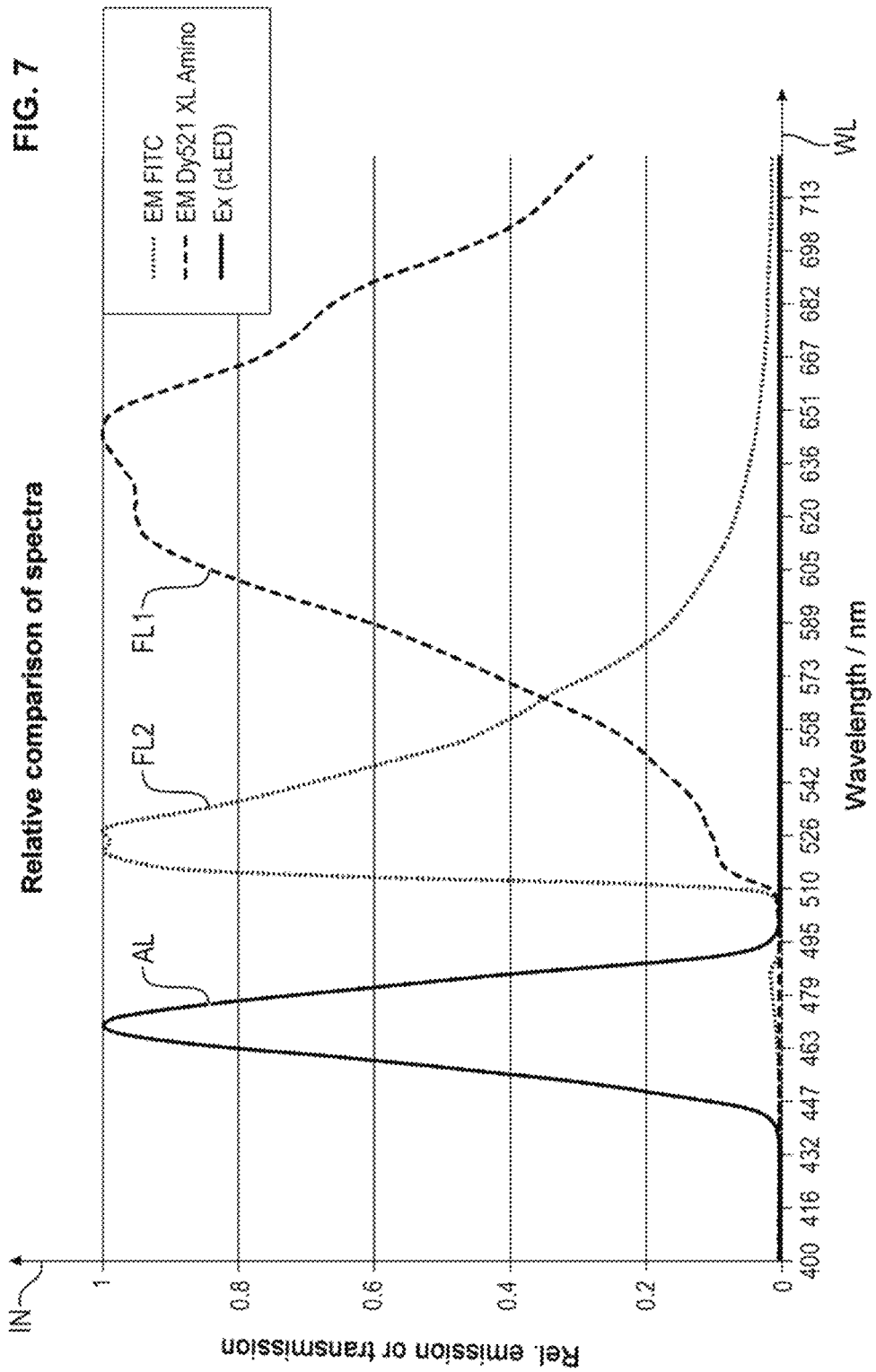

BI12

BI12

METHOD FOR AUTOMATED DETECTION OF ANTIBODIES IN A LIQUID BIOLOGICAL SAMPLE USING AN ANTIGEN CHIP, AND ANTIGEN CHIP THEREFOR

CROSS-REFERENCE TO RELATED APPLICATIONS

This application is the National Stage entry under § 371 of International Application No. PCT/EP2019/065874, filed on Jun. 17, 2019, and which claims the benefit of European Application No. 18182266.9, filed on Jul. 6, 2018. The content of each of these applications is hereby incorporated by reference in its entirety.

BACKGROUND OF THE INVENTION

Field of the Invention

The invention relates to a method for automated detection of antibodies in a liquid biological sample by means of use of an antigen chip and to a corresponding antigen chip therefor.

The invention further relates to a method for automated image processing for detection of antibodies in a liquid biological sample.

Description of Related Art

Diagnostic methods in which a presence of antibodies in a liquid biological sample such as, for example, blood serum is detected by means of antigens are known. To this end, use is made of substrates, also called chips, on the surface of which antigens are applied in the form of gel drops or spots. After application, the drops or spots dry on the surface of the substrate. To detect whether antibodies of a particular type are present in a liquid biological patient sample, the spots are first incubated with the sample, it then being possible for antibodies to bind to antigens depending on the type of antigens and the type of antibodies. The antibodies of the sample are sometimes also referred to as first antibody in such a method. What then subsequently takes place is an incubation of the spots with a conjugate comprising second antibodies which are in turn labeled with a dye. The second antibodies then bind to the first antibodies, with the result that it is then possible, by means of detection of a color of the spots due to the dye, to indirectly detect binding of the first antibodies to the antigens in order to obtain information about whether first antibodies of a particular type are or were present in the sample. Here, the dye can, for example, be a fluorescent dye.

WO 2012/094427 A1 discloses methods for fluorescence detection of antibodies by fluorescence detection. US 2005/0124017 discloses fluorescence imaging for detection of proteins, antibodies, drugs or other ligands in a sample, involving scanning of an image. US 2004/0253640 discloses a microarray with proteins printed thereon for detection of a target protein by immunofluorescence. WO 2017/025954 A1 discloses an antigen chip for immunofluorescence detection, the antigen chip being scanned for the purpose of detection. WO 2012/052994 A2 discloses microarrays for high-throughput characterization of the immune response. WO 2012/037369 A discloses antibody detection by fluorescence detection. WO 2004/027379 A discloses a rolling-beads technique for detection of primary antibodies bound on an antigen microarray. WO 2000/063701 A2 discloses microarrays of polypeptides for detection of, for example, antibodies, fluorescence detection being used and the microarrays being scanned. WO 2011/101487 A1 discloses a method for disease diagnosis via simultaneous detection of antibodies bound to synthetic and cellular substrates, the antibodies being detected by indirect immunofluorescence. A synthetic substrate is a microparticle or a bead coated with a purified native antigen or a recombinant antigen, and a fluorescence microscope is equipped with a camera and with a scanning system. EP 2 362 222 discloses a method for disease diagnosis, involving simultaneous detection of antibodies bound to cellular or tissue substrates or bound to synthetic substrates, such as, for instance, microparticles or beads coated with the specific antigens. This involves using multicolor fluorescence microscopy for detection of the bound antibodies, the substrates and the bound antibodies having different fluorescent colors.

It is known from the prior art, such as, for example, U.S. Pat. No. 2,017,001 60 52, that antigen spots can comprise a so-called first dye, which becomes visible in a first color channel. The dye used to label the second antibody is then referred to as a so-called second dye, which in turn becomes visible in a second color channel. Here, position identification is achieved in the prior art by arranging all spots in the form of a regular grid corresponding to a chessboard pattern, with different spots comprising different antigens. On the basis of the first dye, the spots can then be identified in terms of position or their location on the substrate in a first image of the first color channel, since the first dye is present or visible irrespective of binding of antibodies of the sample with antigens of the spots. In the first image of the first color channel, it is therefore possible to identify all spots comprising the first dye in terms of their position or in terms of location. On the basis of the first image, a grid is then aligned with respect to the image or with respect to all spots such that the individual fields of the grid each encompass exactly one spot. Thus, this rigid grid requires, in all fields, an exact alignment with respect to the spots of the one rigid pattern. Once the grid has been matched to the first image, the individual grid position or the individual field position within the grid can then be used to respectively establish or specify, on the basis of an associated data information item, which particular identified spot from which particular field bears which exact antigen. Thus, a particular antigen spot comprising a particular antigen must always be exactly identified in a particular field of the grid in order to be able to perform such an antigen assignment without any errors. A position information item for a spot, as gained in the image of the first color channel, can then be used to establish, on the basis of an image of the second color channel, whether a color due to the second dye at precisely that position indicates binding of first antibodies to a particular antigen type.

FIG. 1 depicts, by way of example, an antigen chip AC known from the prior art with antigen spots AS for a recorded image region B for a first color channel or first dye. Likewise depicted is a grid R to be generated or to be identified. The chip AC bears a spot pattern SM. It is assumed that the antigen spot ASX bears a different antigen from the antigen spot ASY. The top-left antigen spot ASX must therefore lie in the top-left field FX of the grid, so that an assignment to a particular antigen can be correctly made.

FIG. 2 shows a configuration in which no accurate or no exact regional arrangement of the spots AS was made on the substrate of the chip AC. Therefore, the spot ASX is only partly present on the chip AC and in the image region B, meaning that although the grid R might be detected per se, a misalignment of the fields FX, FY with respect to the spots ASX, ASY may occur. Therefore, an assignment of an antigen type to the spot ASY on the basis of the grid field FX assigned to the spot ASY would be incorrect, and so would detection of binding with regard to binding of antibodies of the biological sample to a particular antigen. This misdetection would especially occur if the entire spot pattern SM were to be repeated in the direction RI in a repetitive manner as part of a production process, meaning that an antigen spot ASX2 bearing the same antigen as the spot ASX would be present. Thus, the entire spot pattern SM would have to be positioned very accurately on the chip AC during a production process in order to avoid misassignment of antigen types to antigen spots ASX, ASY, ASZ. The prior art thus requires high precision in connection with producing the substrate or antigen chip bearing different antigen spots comprising different antigen types. The antigen chip known from the prior art is furthermore sensitive to position deviation of antigen spots, such as, for example, of the spots ASZ, ASW of the pattern SM.

SUMMARY OF THE INVENTION

What is therefore proposed is a method according to the invention for automated detection of antibodies in a liquid biological sample by means of use of an antigen chip and a corresponding antigen chip according to the invention.

The invention further relates to a device for automated image processing for detection of antibodies in a liquid biological sample.

The invention further relates to a data network device for automated image processing for detection of antibodies in a liquid biological sample.

The invention further relates to a computer program product comprising commands which, upon execution of the program by a computer, prompt said computer to carry out a method for automated image processing for detection of antibodies in a liquid biological sample.

The invention further relates to a data carrier signal which transmits the computer program product.

The invention further relates to a method for producing an antigen chip.

The invention further relates to a slide comprising a plurality of antigen chips.

The invention further relates to a kit for use in a method for detection of antibodies in a sample, comprising at least one antigen chip.

In the context of this application, a liquid, biological sample can also be referred to as a liquid patient sample from a patient. An example of a liquid patient sample is a liquid patient sample comprising blood constituents. In particular, the liquid patient sample can be a blood serum.

The present invention also includes the following embodiments:
1. An antigen chip (A2, A11, A12, A21, A22)
   having a level substrate surface (SO) with antigen spots (AS) which are applied thereon and spaced apart and which comprise an identical, common dye,
   the antigen spots (AS) forming respective antigen spot sets (AG) which form corresponding respective, regular antigen spot patterns (AM, AM1, AM2),
   wherein antigen spots (AS) of a same antigen spot set comprise an identical, common antigen type and wherein two or more of the antigen spot sets (A1, A2) comprise different antigen types,
   wherein reference spots (RS) are furthermore applied on the substrate surface (SO), the reference spots forming a reference spot set, which forms a regular reference pattern (RM),
   wherein furthermore the reference pattern differs with respect to its regularity from the antigen spot patterns,
   the reference spots (RS) likewise comprising the identical, common dye.
2. The antigen chip (A2, A11, A12, A21, A22) as in embodiment 1,
   wherein the reference pattern (RM) differs with respect to its regularity from the antigen spot patterns (AM, AM1, AM2) by one or more of the following criteria:
   within the reference pattern (RM) and within the antigen spot patterns (AM, AM1, AM2), the respectively associated spots follow one another at respective regular distances (SD1, SD2), wherein the regular distance (SD1) of the reference spots (RS) of the reference pattern (RM) differs from the regular distances (SD2) of the antigen spots of the antigen spot patterns (AM, AM1, AM2);
   the reference pattern (RM) has, in relation to an immediately adjacent pattern, such a neighboring distance which differs from the other neighboring distances of the antigen spot patterns;
   within the reference pattern (RM) and within the antigen spot patterns (AM, AM1, AM2), the respectively associated spots have a respective, identical size, such that the size of the reference spots of the reference pattern (RM) differs from the sizes of the antigen spots of the antigen spot patterns (AM, AM1, AM2).
3. The antigen chip (A2, A11, A12, A21, A22) as in embodiments 1 or 2,
   wherein the reference pattern (RM) and the antigen patterns (AM, AM1, AM2) are arranged along an arrangement direction (ANR) of the patterns,
   and wherein the reference pattern (RM) and the antigen patterns (AM, AM1, AM2) have respective spreading directions (ABR) which run substantially perpendicularly to the arrangement direction (ANR) of the patterns (RM, AM, AM1, AM2).
4. The antigen chip (A2, A11, A12, A21, A22) as in embodiments 1 or 2,
   wherein the reference spots of the reference spot set form a reference line pattern (RM) and wherein furthermore the respective antigen spots of the respective antigen spot sets form respective antigen line patterns (AM, AM1, AM2),
   the line patterns running substantially parallel to one another.
5. The antigen chip (A2, A11, A12, A21, A22) as in embodiment 1,
   wherein the identical, common dye is a fluorescent dye.
6. The antigen chip (A2, A11, A12, A21, A22) as in embodiment 1,
   wherein the second dye is a fluorescent dye.
7. The antigen chip (A2, A11, A12, A21, A22) as in embodiments 1 to 6,
   wherein the reference spots (RS) of the reference spot set comprise the dye in a dye concentration greater than the dye concentrations in which the antigen spots of the antigen spot sets (AM, AM1, AM2) comprise the dye.
8. The antigen chip (A2, A11, A12) as in any of embodiments 1 to 5, the reference spots (RS) being first reference spots which form a first reference spot set which in turn forms a first regular reference pattern (RM), wherein second reference spots form a second reference spot set which in turn forms a second regular reference pattern (RM2), the second reference spots likewise comprising the identical, common dye, furthermore wherein the second reference pattern (RM2) differs with respect to its regularity from the antigen spot patterns (AM, AM1, AM2) of the antigen spot sets and additionally also from the first reference pattern (RM) of the first reference spots.

9. The antigen chip as in any of embodiments 1 to 6, wherein the reference spots (RS) comprise furthermore an antigen.

10. The antigen chip as in any of embodiments 1 to 6, wherein the reference spots (RS) comprise furthermore an antibody, especially IgG.

11. A method for automated detection of antibodies in a liquid biological sample by means of use of an antigen chip (A2, A11, A12, A21, A22), comprising the steps of providing an antigen chip (A2, A11, A12, A21, A22) as in any of embodiments 1 to 10, (S1)

incubating the spots of the antigen chip (A2, A11, A12, A21, A22) with the biological sample, (S2)

incubating the spots with a conjugate which comprises a secondary antibody labeled with a second dye, (S3)

acquiring or providing at least one first image information item (BI1, BI11) which represents a color of the reference spots and of the antigen spots due to the first dye, (S4)

detecting the reference pattern (RM) and an associated reference position on the basis of the at least one first image information item (BI1, BI11), (S5)

detecting the respective antigen spot patterns (AM, AM1, AM2) and respective associated further positions on the basis of the at least one first image information item (BI1, BI11), (S6)

generating an assignment information item (ZI), which indicates an assignment of the respective antigen spot patterns (AM, AM1, AM2) to respective antigen types, on the basis of the detected reference position and the detected further positions, (S7)

acquiring or providing a second image information item (BI2, BI12) which represents a potential color of the antigen spots due to the second dye, (S8)

determining respective measures of binding which indicate respective bindings of antibodies of the biological sample to respective antigen types on the basis of the second image information item (BI2, BI12) and the assignment information item (ZI). (S9)

12. A method for automated image processing for detection of antibodies in a liquid biological sample, comprising providing or acquiring a first image information item (BI1, BI11) which represents a color of reference spots and of antigen spots of an antigen chip (A2, A11, A12, A21, A22) as in any of embodiments 1 to 10 due to a first dye, (S4)

detecting the reference pattern (RM) and an associated reference position, (S5)

detecting the respective antigen spot patterns (AM, AM1, AM2) and respective associated further positions on the basis of the at least one first image information item (BI1, BI11), (S6)

generating an assignment information item (ZI), which indicates an assignment of the respective antigen spot patterns to respective antigen types, on the basis of the detected reference position and the detected further positions, (S7)

providing or acquiring a second image information item (BI2, BI12) which represents a potential color of the antigen spots of the antigen chip (A2, A11, A12, A21, A22) due to a second dye after incubation of the spots of the antigen chip with the biological sample and with a conjugate which comprises a secondary antibody labeled with the second dye, (S8)

determining respective measures of binding which indicate respective bindings of antibodies of the biological sample to respective antigen types on the basis of the second image information item (BI2, BI12). (S9)

13. The method as in embodiments 11 or 12, the antigen chip being an antigen chip as in embodiment 8, the reference position being a first reference position, further comprising:

detecting the second reference pattern (RM2) and a second associated reference position on the basis of the first image information item (BI1, BI11), generating the assignment information item (ZI), which indicates the assignment of the respective antigen spot patterns to the respective antigen types, on the basis of the detected first reference position, the detected second reference position and the detected further positions.

14. The method as in embodiments 11 or 12, wherein the assignment of the respective detected antigen spot patterns to respective antigen types is achieved by determining a spatial sequence of the reference position and of the further positions, providing a sequence data set (ADS) which indicates a sequence of antigen types, generating the assignment information item (ZI), which indicates the assignment of the respective antigen spot patterns to the respective antigen types, on the basis of the detected reference position, the detected further positions and the sequence data set (ADS).

15. The method as in embodiment 12, wherein the first image information item (BI1, BI11) is received via at least one data interface (DS) and is provided by means of at least one storage unit (MEM)

and wherein the second image information item (BI2, BI12) is received via the data interface (DS) and is provided by means of the storage unit (MEM).

16. A method for producing an antigen chip (A2, A11, A12, A21, A22) for immunodiagnostics, comprising providing a substrate having a level substrate surface (SO), applying reference spots (RS) to the level substrate surface (SO), and applying antigen spots (AS) to the level substrate surface (SO), the application of the reference spots and of the antigen spots (AS) being carried out such that the reference spots (RS) and the antigen spots (AS) of the antigen chip (A2, A11, A12, A21, A22) are realized as per an antigen chip as in any of embodiments 1 to 10.

17. The method as in embodiment 16,
further comprising: fragmenting the substrate (SU) in order to obtain multiple antigen chips (A11, A12).
18. The method as in embodiments 16 or 17,
wherein the substrate surface (SO) is a surface of a glass substrate or of a glass substrate coated with a membrane and/or film.
19. A device (V1) for automated image processing for detection of antibodies in a liquid biological sample, comprising
at least one image acquisition unit (K1, K2)
for acquiring a first image information item (BI1, BI11) which represents a color of reference spots (RS) and of antigen spots (AS) of an antigen chip (A2, A11, A12, A21, A22) as in any of embodiments 1 to 10 due to a first dye,
and furthermore for acquiring a second image information item (BI2, BI12) which represents a potential color of the antigen spots (AS) of the antigen chip (A2, A11, A12, A21, A22) as in any of embodiments 1 to 10 due to a second dye after incubation of the spots of the antigen chip with the biological sample and with a conjugate which comprises a secondary antibody labeled with the second dye,
and furthermore at least one computing unit (R) which is designed
to detect the reference pattern (RM) and an associated reference position on the basis of the at least one first image information item (BI1, BI11),
to detect the respective antigen spot patterns (AM) and respective associated further positions on the basis of the at least one first image information item (BI1, BI11),
to generate an assignment information item (ZI), which indicates an assignment of the respective antigen spot patterns to respective antigen types, on the basis of the detected reference position and the detected further positions,
and to determine respective measures of binding which indicate respective bindings of antibodies of the biological sample to respective antigen types on the basis of the second image information item (BI2, BI12).
20. The device as in embodiment 19,
further comprising
at least one illumination unit (FL) for emitting excitation light (AL) for exciting an emission of first fluorescence radiation of a first wavelength range due to the first dye.
21. The device as in embodiment 19,
further comprising
at least one illumination unit (FL) for emitting excitation light (AL) for exciting an emission of second fluorescence radiation of a second wavelength range due to the second dye.
22. A data network device (V2) for automated image processing for detection of antibodies in a liquid biological sample, comprising
at least one data interface (DS)
for receiving a first image information item (BI1, BI11) which represents a color of reference spots (RS) and of antigen spots (AS) of an antigen chip (A2, A11, A12, A21, A22) as in any of embodiments 1 to 10 due to a first dye,
and furthermore for receiving a second image information item (BI2, BI12) which represents a potential color of the antigen spots (AS) of the antigen chip (A2, A11, A12, A21, A22) as in any of embodiments 1 to 10 due to a second dye after incubation of the spots of the antigen chip with the biological sample and with a conjugate which comprises a secondary antibody labeled with the second dye,
and furthermore at least one computing unit (R2) which is designed
to detect the reference pattern (RM) and an associated reference position on the basis of the at least one first image information item (BI1, BI11),
to detect the respective antigen spot patterns (AM, AM1, AM2) and respective associated further positions on the basis of the at least one first image information item (BI2, BI12),
to generate an assignment information item (ZI), which indicates an assignment of the respective antigen spot patterns to respective antigen types, on the basis of the detected reference position and the detected further positions,
and to determine respective measures of binding which indicate respective bindings of antibodies of the biological sample to respective antigen types on the basis of the second image information item (BI2, BI12).
23. A computer program product
comprising commands which, upon execution of the program by a computer, prompts said computer to carry out a method as in any of embodiments 12 to 15.
24. A data carrier signal which transmits the computer program product as in embodiment 23.
25. A slide (OT)
comprising a multiplicity of antigen chips (A) as in any of embodiments 1 to 10.
26. A kit for use in a method for detection of antibodies in a sample, comprising:
at least one antigen chip (A2, A11, A12, A21, A22) as in any of embodiments 1 to 10,
and furthermore a conjugate which comprises a secondary antibody labeled with a second dye.
27. The kit as in embodiment 26,
wherein the second dye is a fluorescent dye, a chromogenic substrate, an enzyme or a substrate for a chemiluminescence reaction.

BRIEF DESCRIPTION OF THE DRAWINGS

FIG. 3A shows exemplary embodiments of an antigen chip according to the invention.
FIG. 3B shows exemplary embodiments of an antigen chip according to the invention.
FIG. 5A shows respective images of an exemplary antigen chip in respective color channels on the basis of a respective color due to respective dyes.
FIG. 5B shows respective images of an exemplary antigen chip in respective color channels on the basis of a respective color due to respective dyes.

FIG. 6 shows an exemplary spectrum of an excitation light and of a fluorescence light.

FIG. 7 shows a further example of a spectrum of an excitation light and also respective fluorescence light spectra of respective fluorescent dyes.

DETAILED DESCRIPTION OF THE INVENTION

Figure 1:
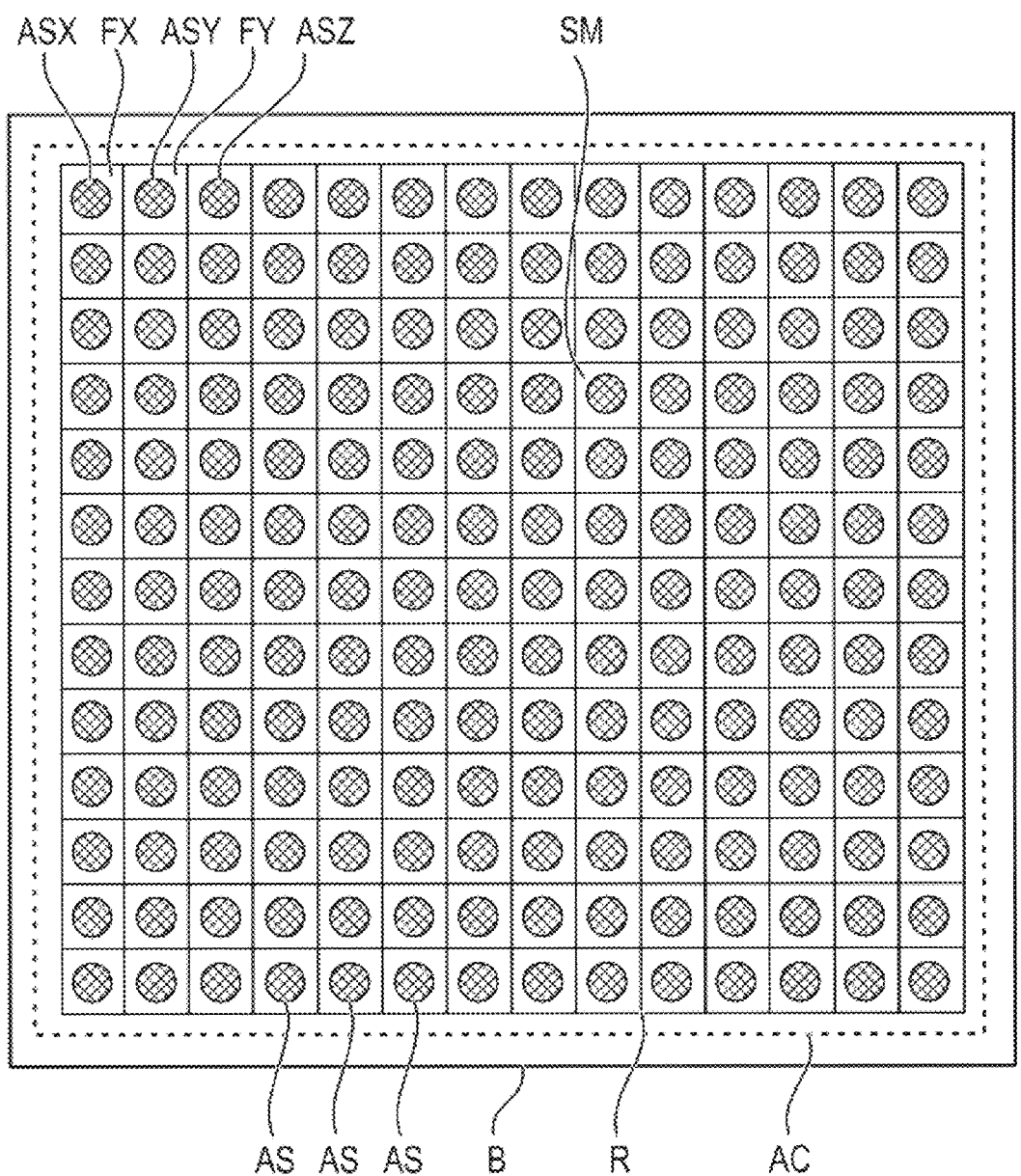
FIG. 1 shows antigen chips from the prior art.

The antigen chip according to the invention has a level substrate surface with antigen spots which are applied thereon and spaced apart and which comprise an identical, common dye. Said dye can also be referred to as a first dye. Here, the antigen spots form respective antigen spot sets which form respective regular antigen spot patterns, wherein antigen spots of a same antigen spot set comprise an identical, common antigen type. Here, two or more of the antigen spot sets comprise different antigen types. The antigen chip according to the invention is characterized in that reference spots likewise comprising the identical, common dye are furthermore applied on the substrate surface. The reference spots form a reference spot set which in turn forms a regular reference pattern, especially along an arrangement direction in which the patterns follow one another. The reference pattern differs with respect to its regularity from the antigen spot patterns or from the regularities of the antigen spot patterns.

The antigen chip according to the invention is then used in the method according to the invention for automated detection of antibodies in a liquid biological sample. Here, the identical, common dye is simply also to be referred to as a first dye. The method first involves incubating the spots of the antigen chips with the biological sample. Furthermore, the spots are incubated with a conjugate which comprises a secondary antibody labeled with a second dye. On particular antigen spots, this can yield the above-described bindings of the secondary antibodies and thus of the second dye too, depending on the type of antigen of an antigen spot and depending on the primary antibody present in the sample. The method then involves acquiring or providing a first image information item which represents a color of the reference spots and of the antigen spots due to the first dye. What then takes place is detection of the reference pattern and of a reference position associated with the reference pattern on the basis of the at least one first image information item. What then takes place furthermore is detection of the respective antigen spot patterns and of respective associated further positions on the basis of the at least one first image information item. What takes place furthermore is generation of an assignment information item, which indicates an assignment of the respective antigen spot patterns to respective antigen types, on the basis of the detected reference position and the detected further positions. What lastly takes place is acquisition or provision of a second image information item which represents a potential color of the antigen spots due to the second dye. What finally takes place is determination of respective measures of binding which indicate respective bindings of antibodies of the biological sample to respective antigen types on the basis of the second image information item and the assignment information item.

In particular, the reference pattern and the antigen patterns are arranged along an arrangement direction of the patterns, wherein furthermore, in particular, the reference pattern and the antigen patterns have respective spreading directions which run substantially perpendicularly to the arrangement direction of the patterns.

The reference pattern and the antigen spot patterns preferably have respective spreading directions which run perpendicularly to an arrangement direction of the patterns. The spreading directions of the patterns preferably run substantially parallel to one another.

On the antigen chip according to the invention, the antigen spots and the reference spots comprise the identical, common dye which is visible in a first color channel, which is preferably a so-called red channel.

The antigen chip according to the invention and the method according to the invention achieve one or more of the advantages now mentioned below, for which detailed explanations follow hereinafter.

Because the antigen chip comprises reference spots which form a distinct regular reference pattern which differs with respect to its regularity from the antigen spot patterns of the antigen spots, it is possible to detect a position or location of the reference pattern in the first color channel or the first image information item. Since the antigen spot patterns differ in their type of pattern or their regularity from the reference pattern, the antigen spot patterns can be detected separately with respect to their position or location on the substrate surface. It is then simply possible to establish which of the antigen spot patterns comprises which antigen type, since the reference position of the reference pattern in relation to further positions of the further antigen spot patterns indicates from where or from which position a sequence of the antigen spot patterns follows on the substrate surface in an arrangement direction of the patterns. Thus, a particular antigen spot pattern having a particular antigen type need not be arranged on a very particular site of the image or the substrate surface. On the contrary, it is sufficient that an antigen spot pattern is arranged in a particular position with respect to the reference position of the reference pattern along an arrangement direction of the patterns. Generation of an assignment information item which indicates an assignment of respective antigen spot patterns to respective antigen types can then, for example, be achieved by providing a data set which indicates such an assignment depending on a position of the antigen spot pattern in relation to a position of the reference pattern. The method according to the invention is particularly robust as a result, since it is only necessary to arrange the antigen spots of a particular antigen spot set as an antigen spot pattern such that the corresponding pattern sufficiently stands out against other patterns, for example in terms of its position. In the case of the solution according to the prior art, the antigen spots do not form distinct regular patterns, but are instead arranged at very different positions in a kind of chessboard method, wherein an assignment of a particular antigen type to spots is simply highly sensitive to the individual alignment of the spots on the substrate surface or on an image.

The antigen chip according to the invention is particularly further advantageous because, as described above, what only matters is the sequence of the reference pattern and of the antigen spot patterns in the arrangement direction or along the arrangement direction of the patterns on the substrate surface, meaning that the reference pattern and the further antigen spot patterns must merely appear after one another along the arrangement direction in an ordered sequence. This has particular advantages in connection with a production process, since, in the case of application of the entirety of the patterns in a periodic, repeating or repetitive manner, the entirety of the patterns thus being repeated after one another periodically, it is subsequently not necessary to separate or fragment the substrate support exactly at that site at which the entirety of the patterns repeats itself in order to produce multiple antigen chips each having the entirety of the patterns. What is only necessary is that all desired antigen spot sets or antigen spot patterns and the reference pattern or reference spot set each occur at least once on the antigen chip to be produced. Such an entirety of the patterns or such a sequence of said antigen spot patterns and the reference pattern is usually yielded via a predetermined distance along the arrangement direction of the patterns on the substrate support. It is simply not necessary to exactly observe said distance in the antigen chip according to the invention; instead, it is simply sufficient when the repetition distance of the entirety of the patterns along the arrangement direction of the patterns is merely not fallen short of in the production of the antigen chip. For example, the substrate surface can simply also be separated or fragmented after such a distance along the arrangement direction that is greater than the repetition distance of the entirety of the patterns in the arrangement direction, within which all different patterns are contained at least once. It is simply sufficient when the distance between two fragmentation sites is greater than the repetition distance of the entirety of the patterns and, furthermore, also smaller than twice the repetition distance of the entirety of the patterns. Here, separation or fragmentation is carried out especially in a direction perpendicular to the arrangement direction of the patterns.

The antigen chip according to the invention and the method according to the invention are further advantageous because a slight misalignment of individual spots within a particular pattern is an effect to which the method according to the invention reacts less sensitively than the prior-art solution in which all spots must fit into a clear defined and rigid pattern with identical distances between all adjacent spots. In the case of the antigen chip according to the invention, it is simply possible that, in the arrangement of the patterns along an arrangement direction following one another on the substrate surface, a spacing of the patterns in relation to one another can also be different between different patterns. For example, if the patterns are identified or detected in the method according to the invention by the regularity of a pattern, where the spots of a corresponding spot set or relevant spot pattern have on average a particular distance from one another, it is possible for a next, adjacent pattern to have, in relation to the preceding pattern, a neighboring distance which can be different compared to another neighboring distance between other patterns. Nevertheless, by image analysis of the antigen chip according to the invention, the method according to the invention can still identify corresponding positions of the patterns robustly and assign the respective spots to the respective antigen types.

With regard to the reference pattern and the antigen patterns, it can be further stated that the regularity of the reference pattern differs from the regularity of the antigen spot patterns in that the patterns, i.e., the reference pattern and the antigen spot patterns, have a common regularity parameter, the value of which differs in the case of the reference pattern from the values of said regularity parameter of the antigen spot patterns.

Preferably, the identical, common dye is a fluorescent dye, which can also be referred to as a first fluorescent dye. Alternatively, the identical, common dye is a chromogenic substrate which, for the purpose of a chromogenic color change, can form a bond with an enzyme which in turn is present in a conjugate, by means of which the spots of the antigen chip can be incubated.

Preferably, the second dye is a fluorescent dye, which can be referred to as a second fluorescent dye.

In one method step, the respective fluorescent dyes can be excited by radiating excitation light of respective different excitation wavelengths or an identical excitation wavelength for emission of respective fluorescence radiation of respective, different fluorescence wavelengths. Here, the excitation light wavelengths for the two fluorescent dyes can overlap or else be identical.

Preferably, the antigen chip is characterized in that the identical, common dye is a fluorescent dye.

Preferably, the antigen chip is characterized in that the second dye is a fluorescent dye.

According to one embodiment, the antigen chip is characterized in that the reference pattern differs with respect to its regularity from the antigen spot patterns by one or more of the following criteria:
  a) within the reference pattern and within the antigen spot patterns, the respectively associated spots follow one another at respectively regular distances, wherein the regular distance of the reference spots of the reference pattern differs from the regular distances of the antigen spots of the antigen spot patterns; here, the regular distance is the regularity parameter of a pattern;
  b) the reference pattern has, in relation to an immediately adjacent pattern, such a neighboring distance which differs from the other neighboring distances of the antigen spot patterns; here, the neighboring distance in relation to an adjacent pattern in the arrangement direction of the patterns is the regularity parameter of a pattern;
  c) within the reference pattern and within the antigen spot patterns, the respectively associated spots have a respective, identical size, such that the size of the reference spots of the reference pattern differs from the sizes of the antigen spots of the antigen spot patterns; here, the identical size of the spots of a pattern is the regularity parameter of a pattern.

According to one embodiment, the antigen chip is characterized in that the reference spots of the reference spot set form a reference line pattern and in that furthermore the respective antigen spots of the respective antigen spot sets form respective antigen line patterns.

According to one embodiment, the antigen chip is characterized in that the reference line pattern differs with respect to its regularity from the antigen line patterns by one or more of the following criteria:
  a) within the reference line pattern and within the antigen line patterns, the respectively associated spots follow one another at respectively regular distances, wherein the regular distance of the reference spots of the reference line pattern differs from the regular distances of the antigen spots of the antigen line patterns;
  b) the reference line pattern has, in relation to an immediately adjacent line pattern, a neighboring distance which differs from the other neighboring distances of the antigen line patterns;
  c) within the reference line pattern and within the antigen line patterns, the respectively associated spots have a respective, identical size, such that the size of the reference spots of the reference line pattern differs from the sizes of the antigen spots of the antigen line patterns;

Preferably, the distance of the antigen spots from one another within a pattern for at least one of the patterns differs from a spacing distance or neighboring distance of the pattern in relation to an adjacent pattern in the arrangement direction of the patterns.

Preferably, the antigen chip is characterized in that the reference spots comprise furthermore an antigen.

Preferably, the antigen chip is characterized in that the reference spots comprise furthermore an antibody, especially IgG.

In connection with the method according to the invention for automated detection of antibodies in a liquid biological sample, what preferably takes place is output of the measures of binding, especially in the form of a data element which is especially output via a data interface.

What is further proposed is a method for automated image processing for detection of antibodies in a liquid biological sample, comprising the steps of
  providing or acquiring a first image information item which represents a color of reference spots and of antigen spots of an antigen chip according to the invention in accordance with any of the presently proposed embodiments due to a first dye,
  detecting the reference pattern and an associated reference position on the basis of the at least one first image information item,
  detecting the respective antigen spot patterns and respective associated further positions on the basis of the at least one first image information item,
  generating an assignment information item, which indicates an assignment of the respective antigen spot patterns to respective antigen types, on the basis of the detected reference position and the detected further positions,
  providing or acquiring a second image information item which represents a potential color of the antigen spots of the antigen chip according to the invention in accordance with any of the presently proposed embodiments due to a second dye after incubation of the antigen chip with the biological sample and with a conjugate which comprises a secondary antibody labeled with the second dye,
  determining respective measures of binding which indicate respective bindings or degrees of binding of antibodies of the biological sample to respective antigen types on the basis of the second image information item.

In connection with the method for automated image processing for detection of antibodies of a liquid biological sample, it is preferred that the first image information item is received via at least one data interface and is provided by means of at least one storage unit and it is further preferred that the second image information item is received via the data interface and is provided by means of the storage unit.

If the antigen chip has the abovementioned first and second reference spots for forming the first regular reference pattern and the second regular reference pattern, further steps are preferably carried out in the method for automated detection of antibodies in a liquid biological sample and in the method for automated image processing for detection of antibodies in a liquid biological sample. Said further steps to be preferably carried out are:
  detecting the second reference pattern and a second associated reference position on the basis of the first image information item,
  generating the assignment information item, which indicates the assignment of the respective antigen spot patterns to the respective antigen types, on the basis of the detected first reference position, the detected second reference position and the detected further positions.

In connection with the method for automated detection of antibodies and the method for automated image processing, the assignment of the respective detected antigen spot patterns to respective antigen types is achieved by means of further steps to be preferably carried out:
  determining a spatial sequence of the reference position and of the further positions
  providing a sequence data set which indicates a sequence of antigen types,
  generating the assignment information item, which indicates the assignment of the respective antigen spot patterns to the respective antigen types, on the basis of the detected reference position, the detected further positions and the sequence data set.

Preferably, further steps are carried out in one or both of the abovementioned methods:
- identifying multiple potential patterns on the basis of the at least one first image information item,
- detecting respective spot distances of spots within the respective identified potential patterns or for the respectively identified, potential patterns,
- selecting one of the identified patterns as the reference pattern on the basis of the detected spot distances, preferably on the basis of a greatest or a smallest spot distance.

Preferably, the patterns of the spots on the antigen chip are configured such that the reference pattern differs from the antigen spot patterns as a result of the reference pattern having in relation to an immediately adjacent pattern, especially along an arrangement direction of the patterns, such a neighboring distance, which can also be referred to as a pattern distance, that differs from the other neighboring distances or pattern distances of the antigen spot patterns.

What then preferably take place in connection with one or both of the abovementioned methods are further steps that are preferably carried out:
- identifying multiple patterns on the basis of the at least one first image information item,
- detecting respective neighboring distances of the identified patterns, especially along an arrangement direction of the patterns, in relation to their respectively next adjacent especially directly or immediately patterns,
- selecting one of the identified patterns as the reference pattern on the basis of the detected neighboring distances.

If the antigen chip is realized such that the spots within the reference pattern and also within the antigen spot patterns follow one another at respectively regular preferably equidistant distances, the regular distance of the reference spots of the reference pattern differing from the regular distances of the antigen spots of the antigen spot patterns, further steps can be preferably carried out in connection with one or both of the mentioned methods:
- identifying multiple patterns on the basis of the at least one first image information item,
- detecting respective spot sizes for the respective identified patterns,
- selecting one of the identified patterns as the reference pattern on the basis of the detected spot sizes.

If the first dye is a fluorescent dye, further steps can be preferably carried out in one or both of the abovementioned methods:
- illuminating the antigen chip with a first excitation light of a first wavelength range for excitation of an emission of first fluorescence radiation due to the first dye, Here, the first image information item preferably represents a color of the reference spots and of the antigen spots of the antigen chip due to the first fluorescence radiation.

If the second dye is a fluorescent dye, further steps can be preferably carried out in one or both of the abovementioned methods:
- illuminating the antigen chip with a second excitation light of a second wavelength range for excitation of an emission of second fluorescence radiation due to the second dye, Here, the second image information item preferably represents a potential color of the antigen spots of the antigen chip due to the second fluorescence radiation.

Preferably, the first excitation light and the second excitation light have an identical excitation wavelength.

What is further proposed is a device for automated detection of antibodies in a sample, comprising at least one image acquisition unit. The image acquisition unit is designed for acquiring a first image information item which represents a color of reference spots and of antigen spots of an antigen chip according to the invention in accordance with any of the presently described embodiments due to a first dye. The image acquisition unit is furthermore designed for acquiring a second image information item which represents a potential color of the antigen spots of the antigen chip according to the invention in accordance with any of the presently described embodiments due to a second dye after incubation of the antigen chip with the biological sample and with a conjugate which comprises a secondary antibody labeled with the second dye. The device further comprises at least one computing unit which is designed
- to detect the reference pattern and an associated reference position on the basis of the at least one first image information item,
- to detect the respective antigen spot patterns and respective associated further positions on the basis of the at least one first image information item,
- to generate an assignment information item, which indicates an assignment of the respective antigen spot patterns to respective antigen types, on the basis of the detected reference position and the detected further positions,
- and to determine respective measures of binding which indicate respective bindings or degrees of binding of antibodies of the biological sample to respective antigen types on the basis of the second image information item.

The device further comprises at least one illumination unit for emitting excitation light for exciting an emission of first fluorescence radiation of a first wavelength range due to the first dye.

The device further comprises at least one illumination unit for emitting excitation light for exciting an emission of second fluorescence radiation of a second wavelength range due to the second dye.

The proposed device for automated detection of antibodies of a sample preferably comprises at least one computing unit which is furthermore designed to preferably carry out further steps which were disclosed or described above in relation to the method for automated detection of antibodies and/or the method for automated image processing.

Preferably, the device for automated detection comprises a data interface via which an information item or different information items can be provided by means of a data element or multiple data elements. This can be one or more of the following information items:
- an information item based on the abovementioned respective measures of binding,
- an information item based on positions of detected patterns,
- an information item based on positions of individual spots,
- an information item based on an assignment of antigen types to antigen spot sets or antigen spot patterns.

What is further proposed is a data network device for automated image evaluation for detection of antibodies in a sample. The data network device is preferably a so-called cloud system. The data network device comprises at least one data interface which is designed for receiving a first image information item which represents a color of reference spots and of antigen spots of an antigen chip according to the invention in accordance with any of the presently proposed embodiments due to a first dye. The data interface is furthermore designed for receiving a second image information item which represents a potential color of the antigen spots of the antigen chip according to the invention in accordance with any of the presently proposed embodiments due to a second dye after incubation of the antigen chip with the biological sample and with a conjugate which comprises a secondary antibody labeled with the second dye.

The data network device further comprises at least one computing unit which is designed
  to detect the reference pattern and an associated reference position on the basis of the at least one first image information item,
  to detect the respective antigen spot patterns and respective associated further positions on the basis of the at least one first image information item,
  to generate an assignment information item, which indicates an assignment of the respective antigen spot patterns to respective antigen types, on the basis of the detected reference position and the detected further positions,
  and to determine respective measures of binding which indicate respective bindings or degrees of binding of antibodies of the biological sample to respective antigen types on the basis of the second image information item.

What is further proposed is a computer program product comprising commands which, upon execution of the program by a computer, prompt said computer to carry out the proposed method for automated image processing according to any of the presently proposed embodiments.

What is further proposed is a data carrier signal which transmits the computer program product. The data carrier signal can, for example, be provided in the form of data packets, especially IP packets. In particular, the data signal is a download data signal for transmitting software, especially a software application.

What is further proposed is a slide comprising a multiplicity of antigen chips according to the invention in accordance with any of the presently described embodiments.

What is further proposed is a method for producing an antigen chip for immunodiagnostics, comprising the steps of
  providing a substrate having a level substrate surface,
  applying reference spots to the level substrate surface, and
  applying antigen spots to the level substrate surface,
the application of the reference spots and of the antigen spots being carried out such that the reference spots and the antigen spots of the antigen chip are realized as per an antigen chip according to the invention in accordance with any of the presently described embodiments.

The production method preferably further comprises the step of fragmenting the substrate in order to obtain multiple antigen chips, especially at two fragmentation sites, the distance of which from one another is greater than a width of the substrate, within which the entirety of reference patterns and antigen patterns is present.

Preferably, the substrate surface is a surface of a glass substrate or of a glass substrate coated with a membrane and/or film.

The application of the antigen spots can be carried out by means of a piezoelectric microdispenser, and the substrate surface can be especially a surface of a glass substrate or of a glass substrate coated with a membrane and/or film. It is thus possible to carry out production using conventional basic materials and production machines.

What is further proposed is a kit for use in a method for detection of antibodies in a liquid, biological sample, comprising an antigen chip according to the invention in accordance with any of the presently described embodiments and furthermore a conjugate which comprises a secondary antibody labeled with a second dye. Preferably, the second dye is a fluorescent dye, a chromogenic substrate, an enzyme or a substrate for a chemiluminescence reaction.

The chip can be understood to be a solid substrate, for instance a glass plate or, for example, silicon plate. The chip can also be made from plastic or else from metal. The chip can be light-transmissive or non-light-transmissive in order to support transmitted-light or reflected-light illumination/detection. The antigen chip can be used in a scanner system or camera system, especially fluorescence microscope, for examining a sample and can then be irradiated with illumination light or excitation light.

According to one embodiment of the present invention, the substrate surface is microstructured for the purpose of focusing. The microstructuring can be realized by a surface treatment (e.g., roughening) and can facilitate focusing onto the substrate surface. Various methods for microstructuring, such as, for example, injection molding, hot stamping or imprint methods, are known in the prior art. What can be applied on the surface are various microstructure markers which can also be used for identification of the antigen chip, for identification of the sample, etc. The antigen substrate (the chip) comprises especially a surface area of a size between 1 mm×1 mm and 2 mm×4 mm.

The expression "chemiluminescence", as used herein, refers to a chemical reaction in which energy is specifically conducted to a molecule, this bringing about electronic excitation thereof and subsequent release of a photon, with emission of visible light as a result. Thermal energy is not required for said reaction. Chemiluminescence thus involves the direct conversion of chemical energy into light energy. Preferably, chemiluminescence arises as a result of the reaction of a luminophore with other compounds. These reactions can be catalyzed by enzymes. In embodiments of the invention that are further preferred, the luminophore is selected from the group consisting of luminol and derivatives thereof, acridine and derivatives thereof, and luciferins. These compounds can be excited for chemiluminescence by various enzymatic reactions. Relevant compounds and reactions are known in the prior art. In embodiments of the invention that are further preferred, the luminophore is luminol or a derivative thereof, light being emitted as a result of a reaction catalyzed by peroxidase, especially horseradish peroxidase (chemiluminescence). In alternative embodiments of the invention, the luminophore is acridine or a derivative thereof, especially an acridinium ester or acridinium sulfonamide, light being emitted as a result of a reaction catalyzed by phosphatase, especially alkaline phosphatase (AP) (chemiluminescence). In further alternative embodiments of the invention, the luminophore is a luciferin, especially D-luciferin, light being emitted as a result of a reaction catalyzed by luciferase (chemiluminescence).

A "chromogenic substrate" in the context of the present invention is a reagent which can be used for measuring enzyme activities. The chromogenic substrate is altered by enzymatic activity such that a direct or indirect product of the enzymatic reaction can be quantified (photometrically). The chromogenic substrate consists, for example, of an oligopeptide to which an azo dye, for example paranitroaniline, is coupled. The peptide imitates the site of cutting, at which the enzyme under investigation cleaves its physiological substrate. The dye is released as a result of the enzyme action. Color development can be quantified photometrically and enzyme activity ascertained via a calibration curve. The chromogenic substrate can, however, also be 5-bromo-4-chloro-3-indolyl phosphate (BCIP) and/or nitro blue tetrazolium chloride (NBT). A chromogenic substrate can, for example, be detected colorimetrically.

The antigens which are present in the various antigen spots can be selected and designed to bind antibodies which form as a consequence of autoimmune diseases, allergies and infectious diseases. In the present test system, this concerns especially antinuclear and/or extractable antinuclear antibodies from the area of connective tissue diseases. In particular, the following antigens (alone or in any combination) can, for example, be present in the antigen spots: RNP/Sm, Sm, Scl-70, Rib.P0, Jo-1, SS-A, SS-B, dsDNA, nucleosomes/chromatin, Cenp-B, RNP A,C,68 kDa, Ro-52, Ku, histones, DFS70. The diagnosable connective tissue diseases can include at least one of the following forms: SLE (systemic lupus erythematosus), PM, DM (myositis), SS (Sjögren's syndrome), CREST syndrome (limited cutaneous form of systemic sclerosis, lcSSc), PSS (progressive systemic sclerosis), MCTD (mixed connective tissue disease, Sharp syndrome), AID (autoimmune induced disease). Various diseases can thus be diagnosed.

Figure 2:
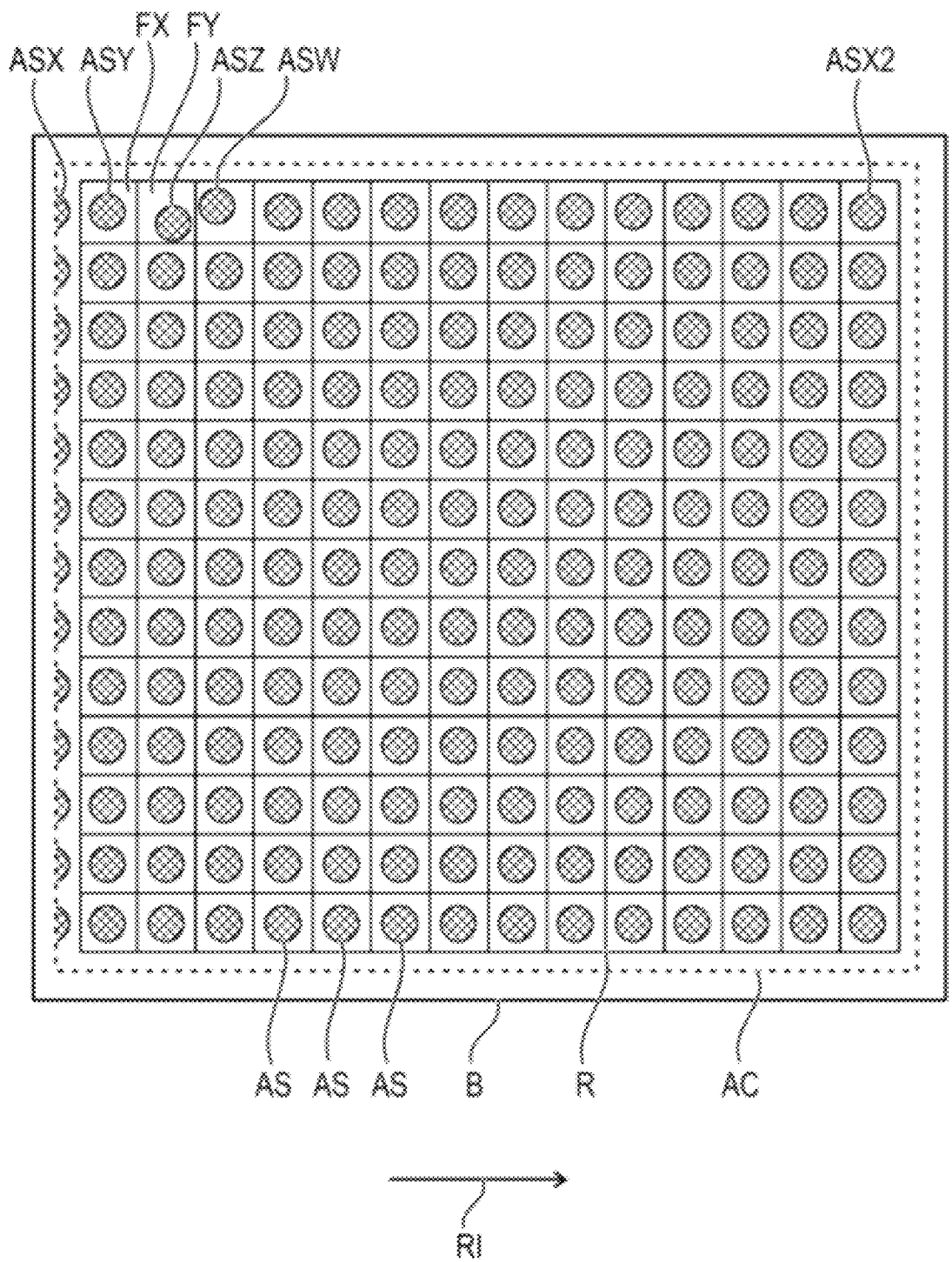
FIG. 2 shows antigen chips from the prior art.
Figure 4A:
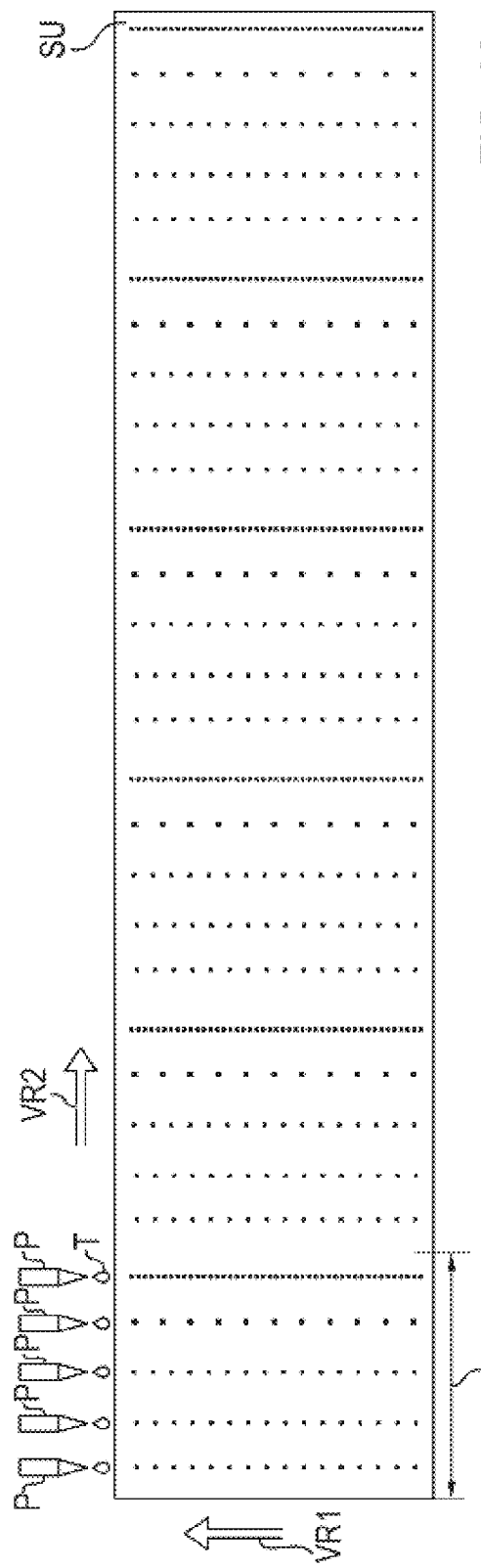
FIG. 4A shows a substrate surface provided with spots for production of an antigen chip according to the invention and also exemplary antigen chips according to the invention.
Figure 4B:
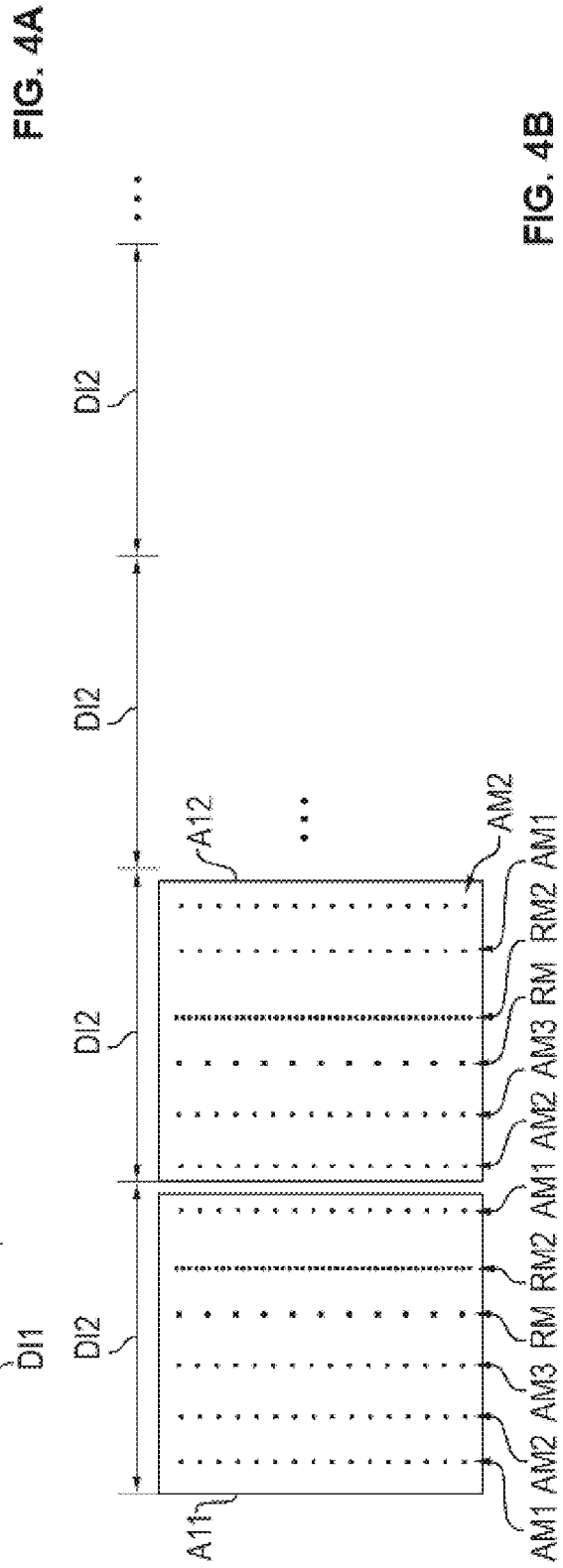
FIG. 4B shows a substrate surface provided with spots for production of an antigen chip according to the invention and also exemplary antigen chips according to the invention.
Figure 8:
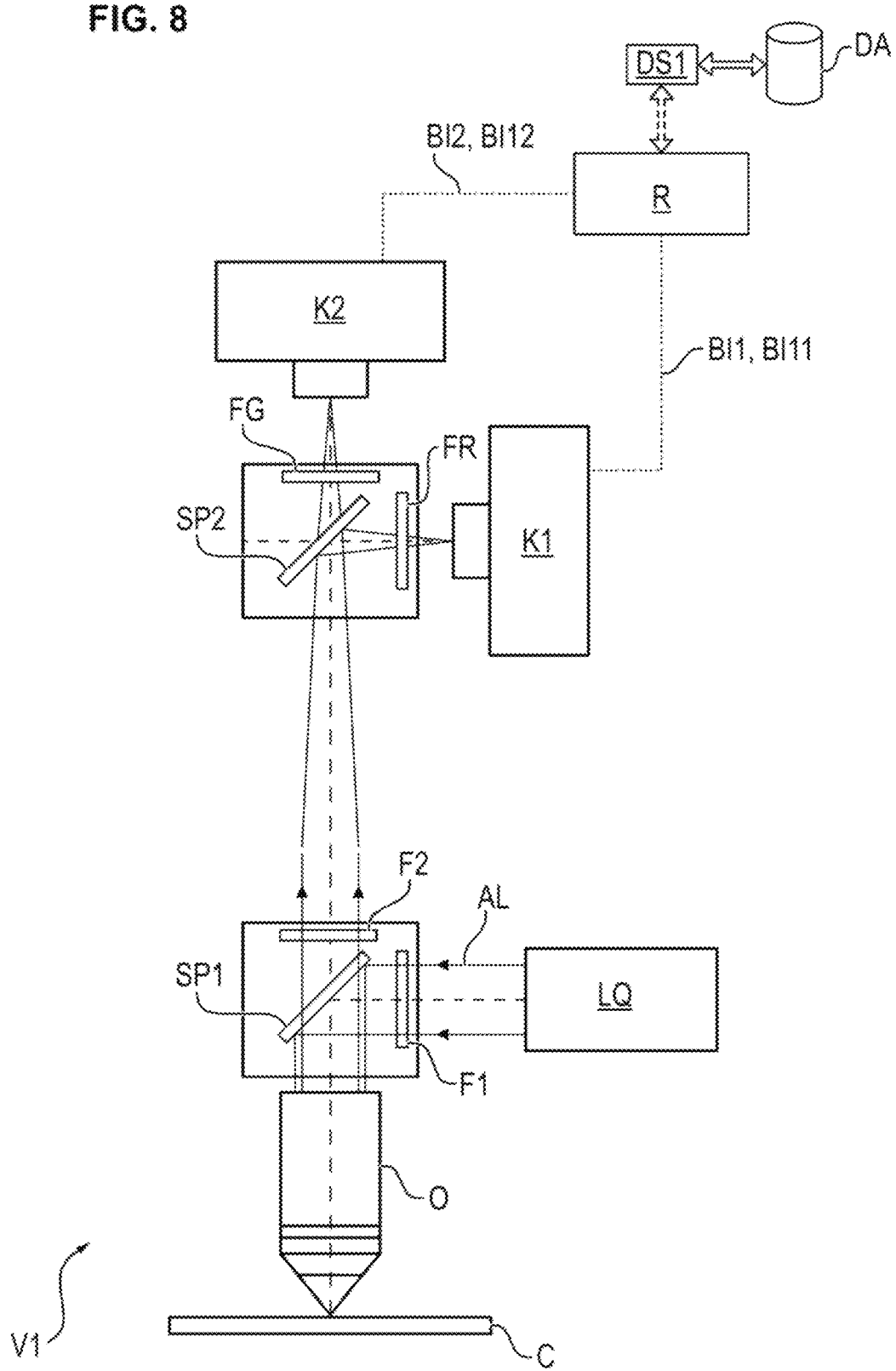
FIG. 8 shows a preferred embodiment of a device according to the invention for automated detection of antibodies in a sample.
Figure 9:
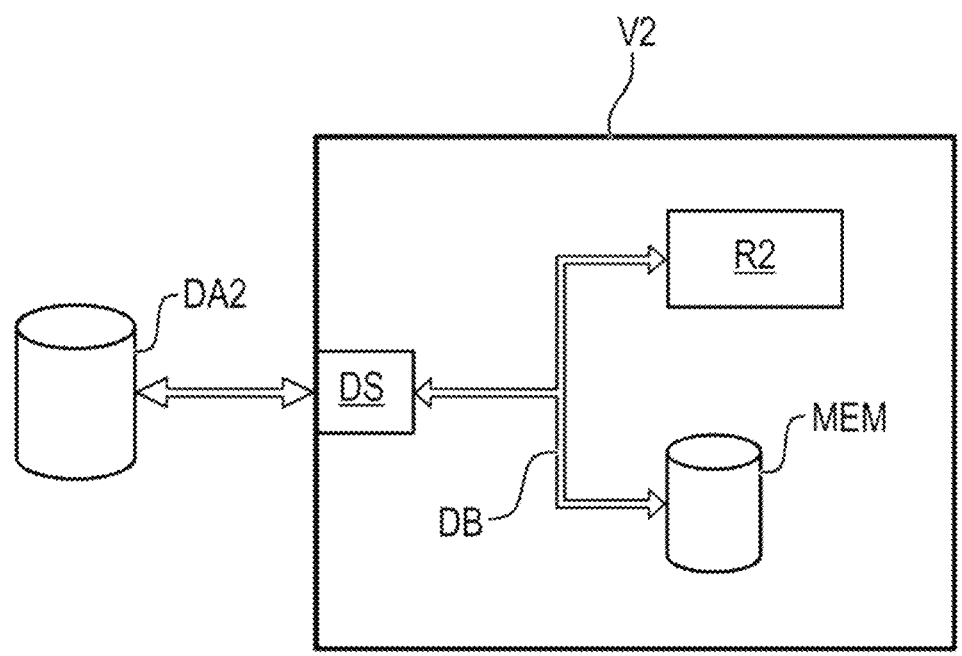
FIG. 9 shows a preferred embodiment of a data network device according to the invention.
Figure 10:
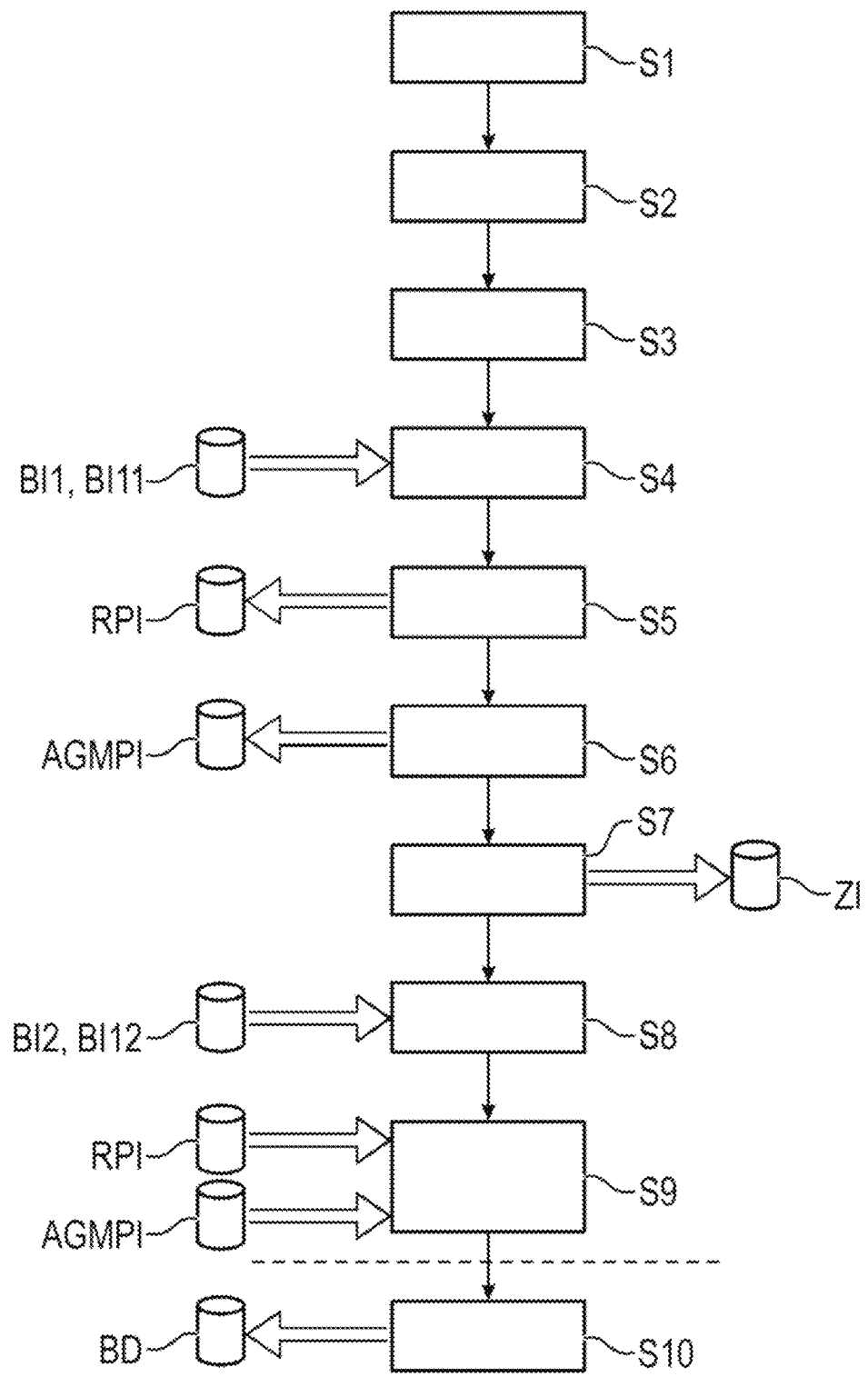
FIG. 10 shows preferred steps for carrying out the method according to the invention for automated detection of antibodies of a liquid, biological sample in accordance with a preferred embodiment.
Figure 11A:
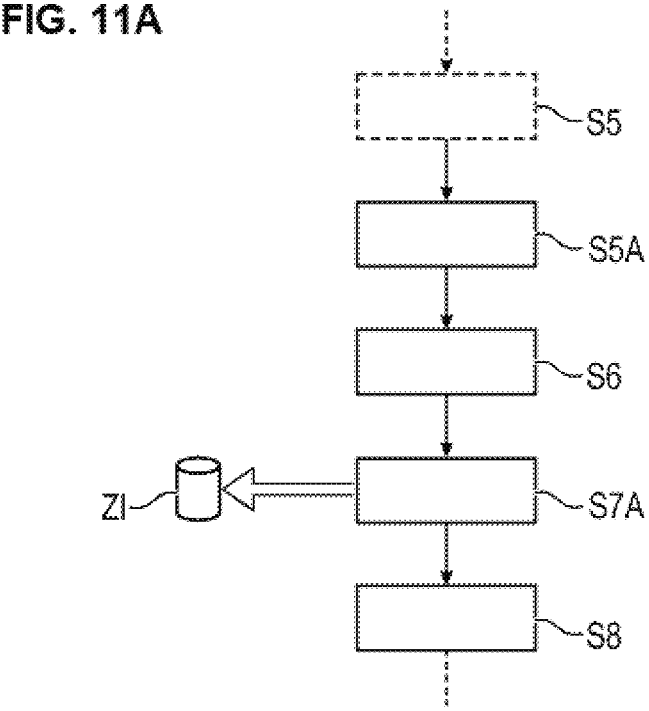
FIG. 11A shows preferred steps in connection with detecting a second reference pattern.
Figure 11B:
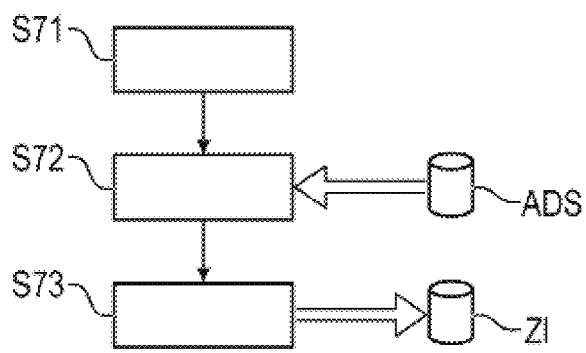
FIG. 11B shows preferred steps in connection with generating an assignment information item.
Figure 11C:
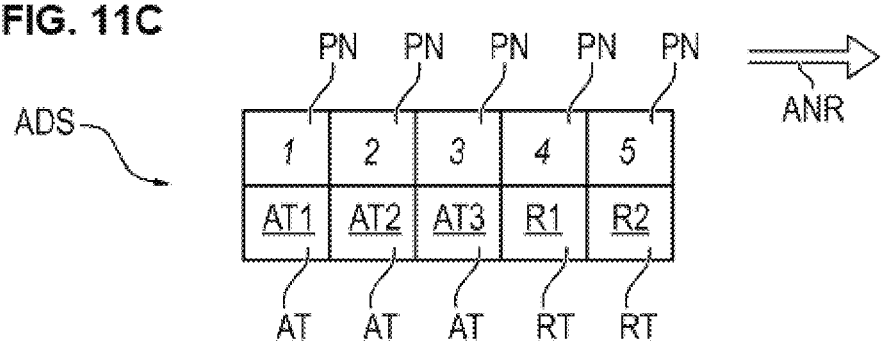
FIG. 11C shows an exemplary embodiment of a sequence data set.
Figure 12:
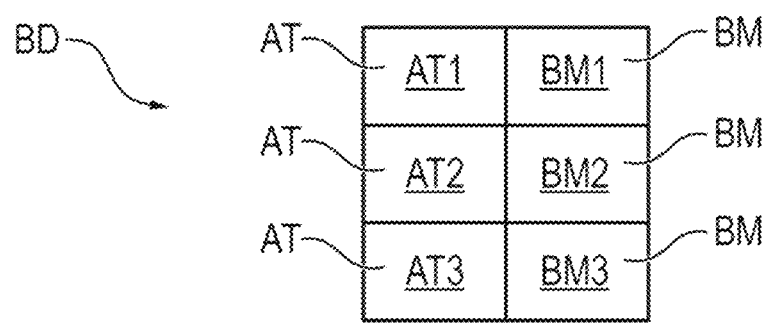
FIG. 12 shows one embodiment of a data set for indicating measures of binding.
Figure 13:
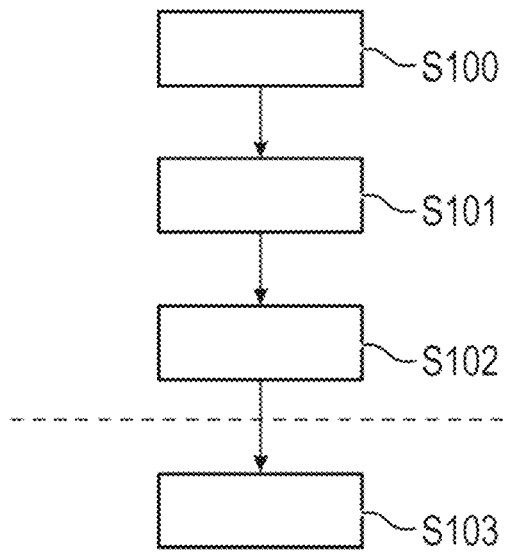
FIG. 13 shows preferred steps to be carried out in connection with a method for producing an antigen chip.
Figure 14:
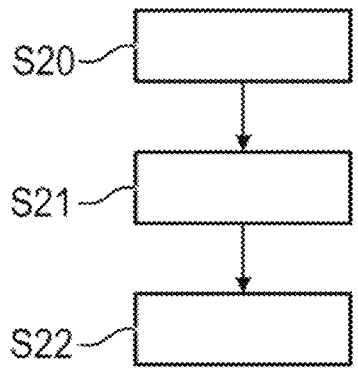
FIG. 14 shows preferred steps to be carried out for detection of a reference pattern and of respective antigen spot patterns.
Figure 15:
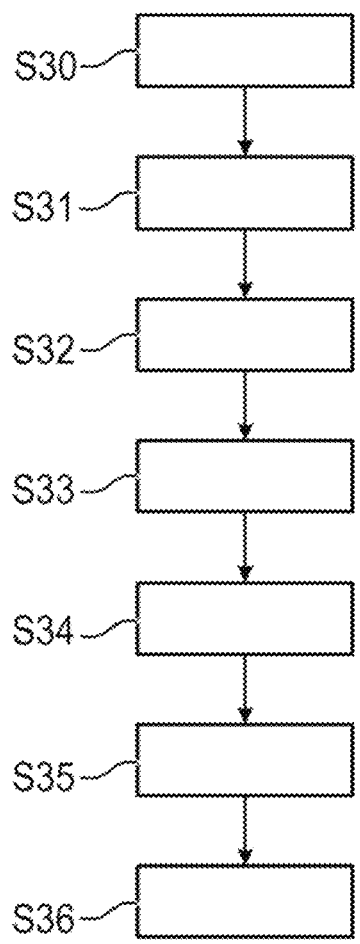
FIG. 15 shows preferred steps to be carried out in connection with identifying multiple potential patterns on the basis of a first image information item and with detecting respective spot distances of spots of patterns.
Figure 16:
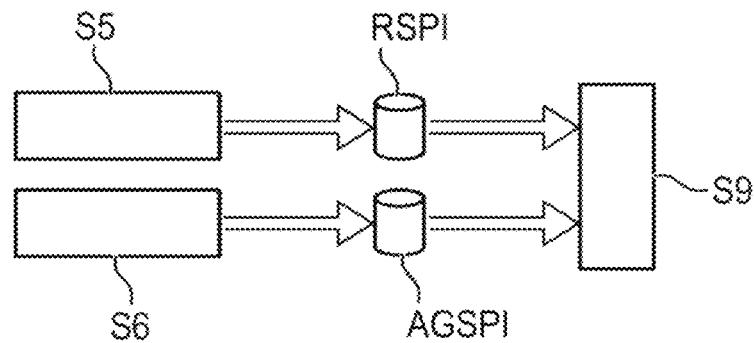
FIG. 16 shows use of position information in connection with determining measures of binding on the basis of a second image information item.
Figure 17:
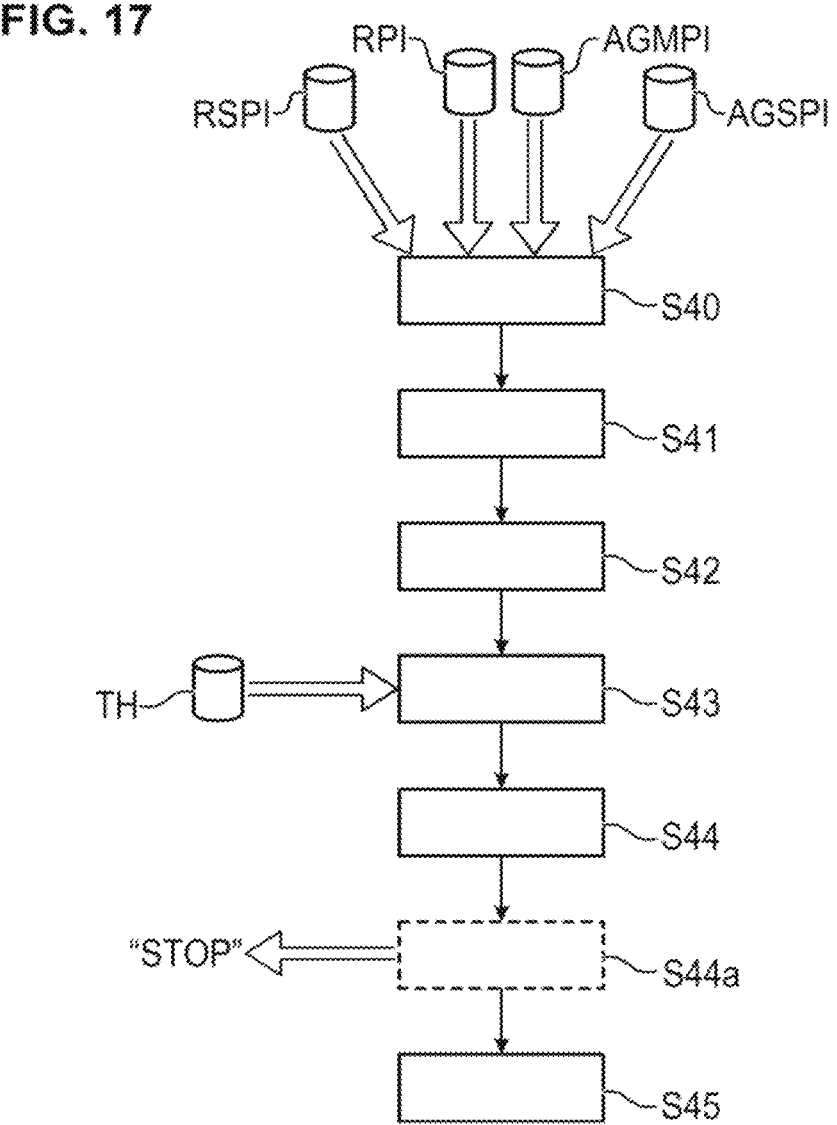
FIG. 17 shows preferred steps to be carried out in connection with the method for automated detection of antibodies or with the method for automated image processing for detection of antibodies.
Figure 18:
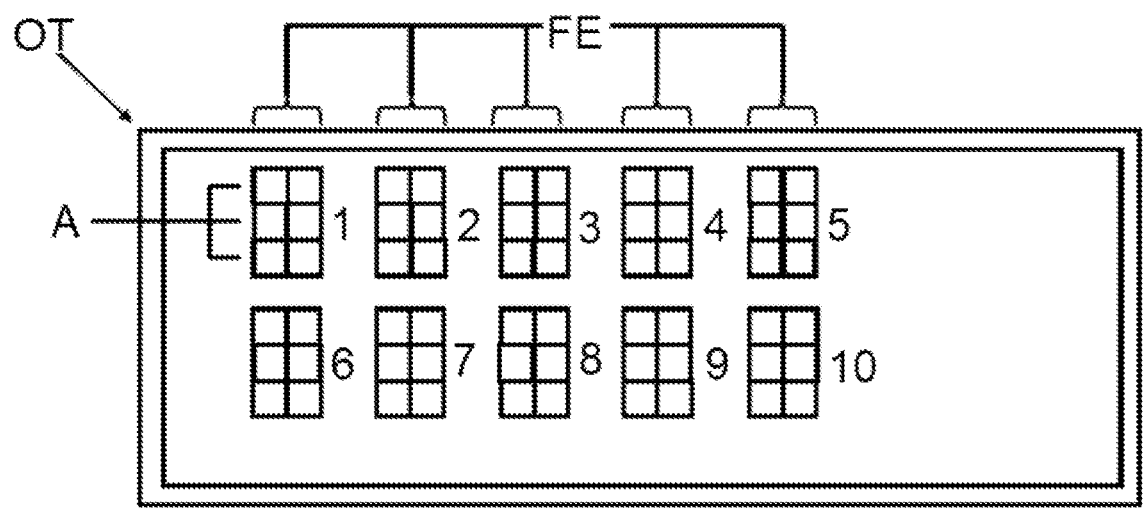
FIG. 18 shows a preferred embodiment of a slide according to the invention comprising a plurality of antigen chips.
Figure 19:
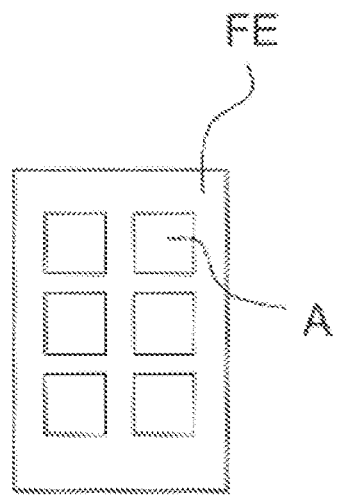
FIG. 19 shows a detailed representation of a field comprising multiple antigen chips.
Figure 20A:
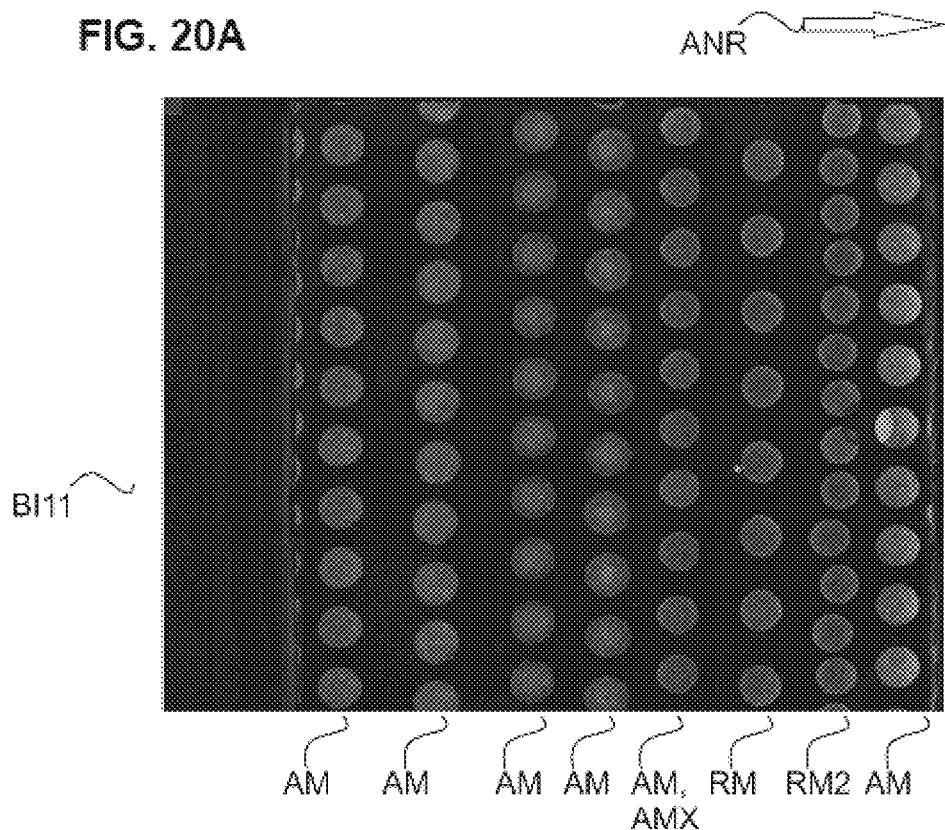
FIG. 20A shows a first image information item or a first image which represents a color of reference spots and antigen spots in a first color channel.
Figure 20B:
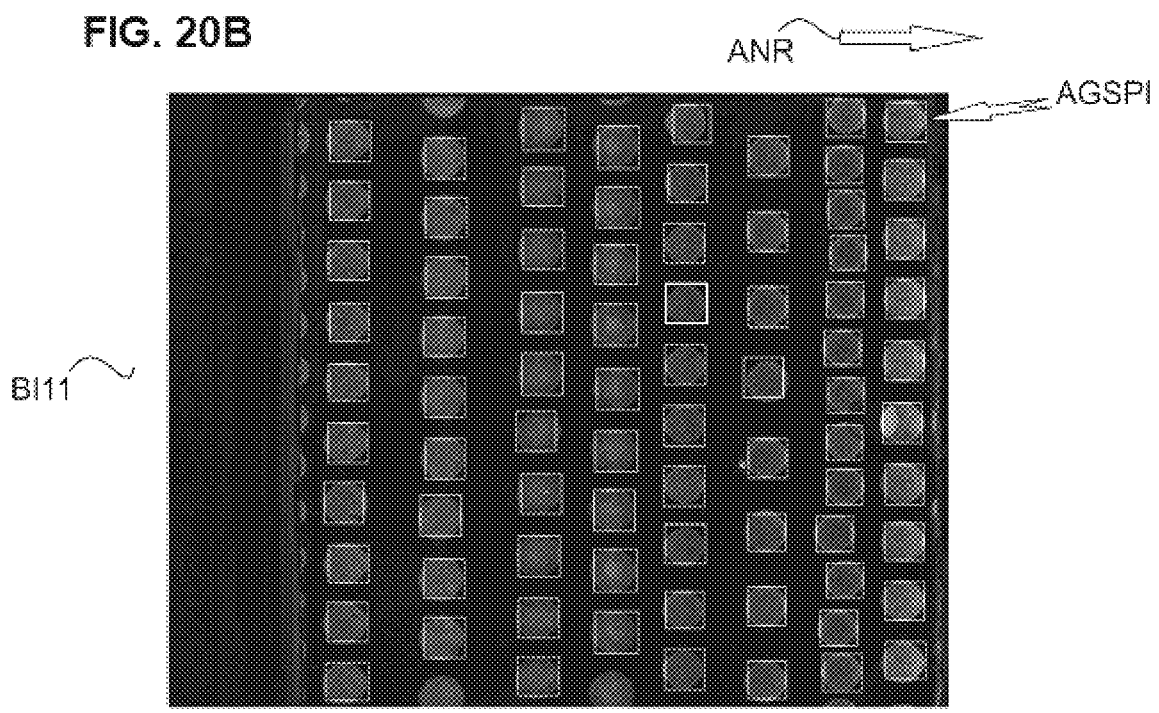
FIG. 20B shows the first image information item or the first image, as shown in FIG. 20A, together with indicated position information of spots.
Figure 21A:
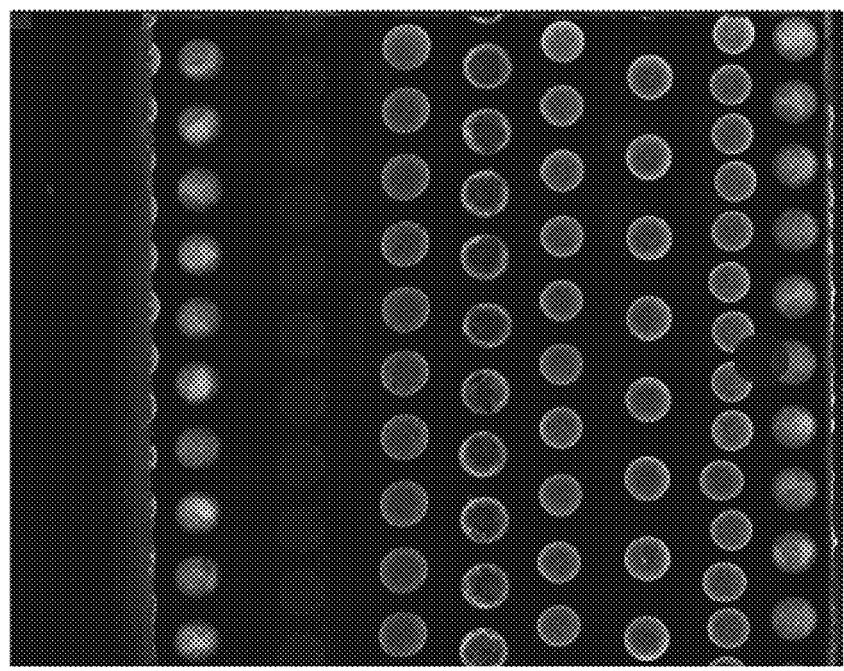
FIG. 21A shows a second image information item or a second image which indicates a color of reference spots and antigen spots in a second color channel.
Figure 21B:
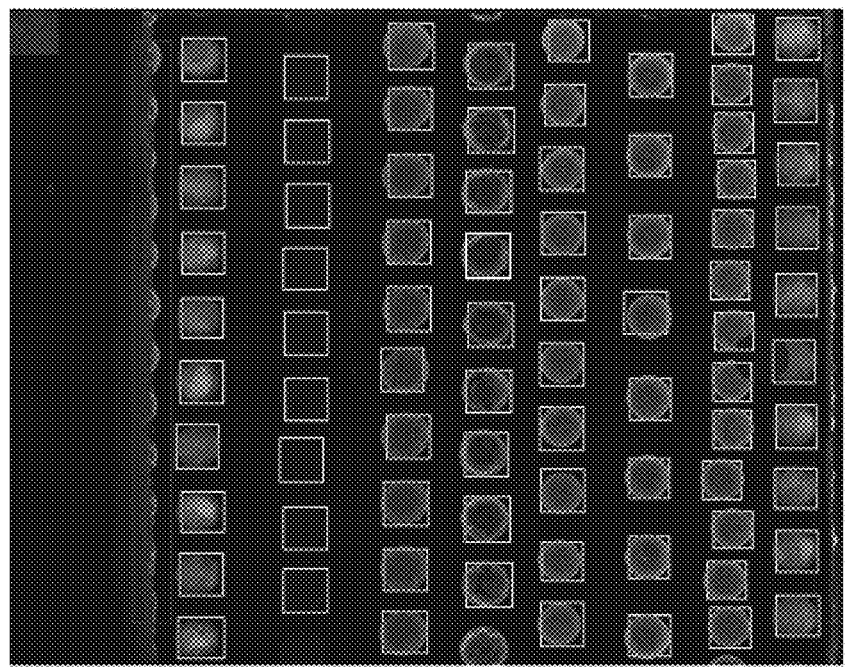
FIG. 21B shows the second image information item or the second image, as shown in FIG. 21A, together with indicated positions of spots, as obtained from the first color channel or the first image information item.
Figure 22A:
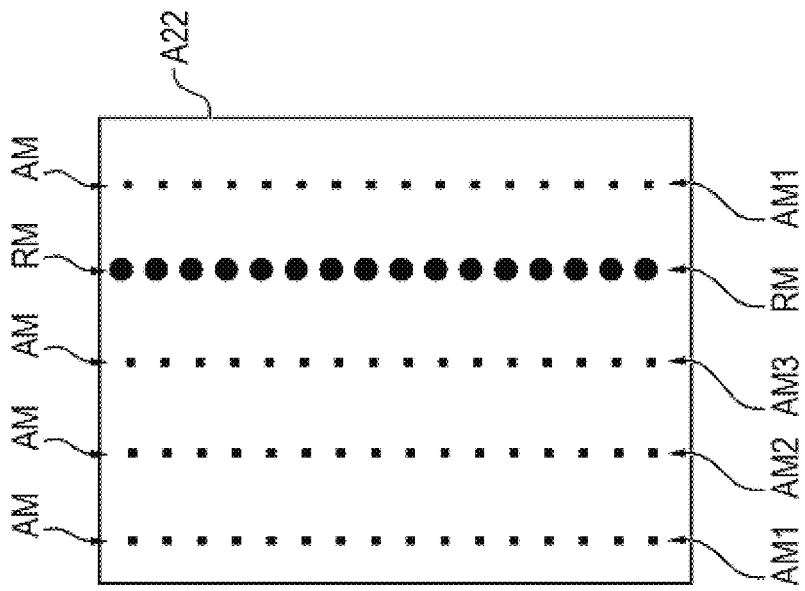
FIG. 22A shows an exemplary embodiment of an antigen chip in which the reference pattern has a different neighboring distance in relation to a next neighboring pattern compared to the antigen spot patterns.
Figure 22B:
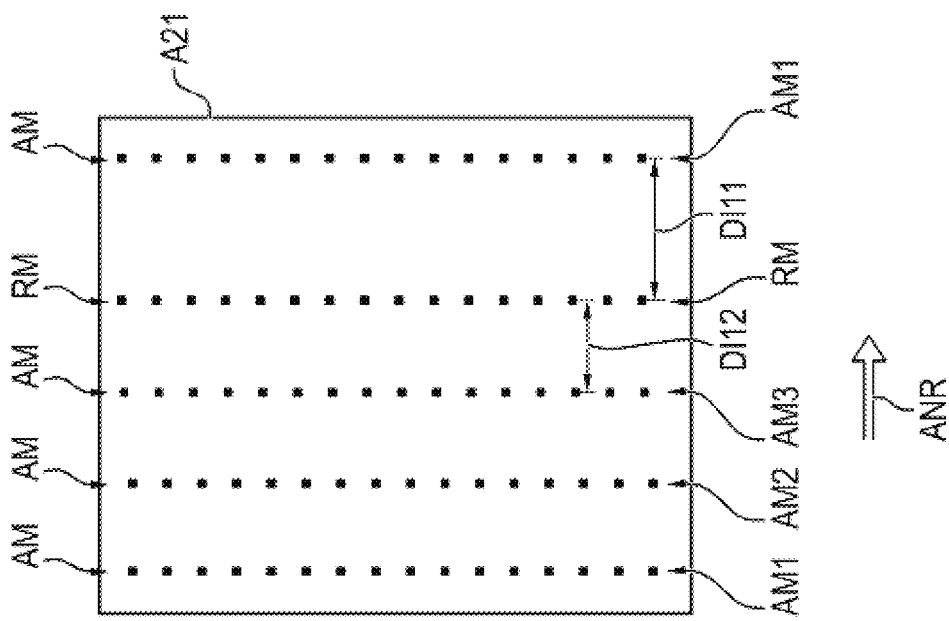
FIG. 22B shows an exemplary embodiment of an antigen chip in which the reference pattern has reference spots of such an identical size which differs from the sizes of the antigen spots of the antigen spot patterns.

Advantageous embodiments of the invention are elucidated in the following description with some reference to the figures, where:

FIGS. 1 and 2 show antigen chips from the prior art,

FIGS. 3A and 3B show exemplary embodiments of an antigen chip according to the invention, FIGS. 4A and 4B show a substrate surface provided with spots for production of an antigen chip according to the invention and also exemplary antigen chips according to the invention, FIGS. 5A and 5B show respective images of an exemplary antigen chip in respective color channels on the basis of a respective color due to respective dyes, FIG. 6 shows an exemplary spectrum of an excitation light and of a fluorescence light, FIG. 7 shows a further example of a spectrum of an excitation light and also respective fluorescence light spectra of respective fluorescent dyes, FIG. 8 shows a preferred embodiment of a device according to the invention for automated detection of antibodies in a sample, FIG. 9 shows a preferred embodiment of a data network device according to the invention, FIG. 10 shows preferred steps for carrying out the method according to the invention for automated detection of antibodies of a liquid, biological sample in accordance with a preferred embodiment, FIG. 11A shows preferred steps in connection with detecting a second reference pattern, FIG. 11B shows preferred steps in connection with generating an assignment information item, FIG. 11C shows an exemplary embodiment of a sequence data set, FIG. 12 shows one embodiment of a data set for indicating measures of binding, FIG. 13 shows preferred steps to be carried out in connection with a method for producing an antigen chip, FIG. 14 shows preferred steps to be carried out for detection of a reference pattern and of respective antigen spot patterns, FIG. 15 shows preferred steps to be carried out in connection with identifying multiple potential patterns on the basis of a first image information item and with detecting respective spot distances of spots of patterns, FIG. 16 shows use of position information in connection with determining measures of binding on the basis of a second image information item, FIG. 17 shows preferred steps to be carried out in connection with the method for automated detection of antibodies or with the method for automated image processing for detection of antibodies, FIG. 18 shows a preferred embodiment of a slide according to the invention comprising a plurality of antigen chips, FIG. 19 shows a detailed representation of a field comprising multiple antigen chips, FIG. 20A shows a first image information item or a first image which represents a color of reference spots and antigen spots in a first color channel, FIG. 20B shows the first image information item or the first image, as shown in FIG. 20A, together with indicated position information of spots, FIG. 21A shows a second image information item or a second image which indicates a color of reference spots and antigen spots in a second color channel, FIG. 21B shows the second image information item or the second image, as shown in FIG. 21A, together with indicated positions of spots, as obtained from the first color channel or the first image information item, FIG. 22A shows an exemplary embodiment of an antigen chip in which the reference pattern has a different neighboring distance in relation to a next neighboring pattern compared to the antigen spot patterns, FIG. 22B shows an exemplary embodiment of an antigen chip in which the reference pattern has reference spots of such an identical size which differs from the sizes of the antigen spots of the antigen spot patterns.

As already explained above, it is known from the prior art to arrange antigen chips with spots of different antigen types in a kind of chessboard pattern. As elucidated above, what can occur here in connection with producing an antigen chip is that an antigen chip AC, as shown in FIG. 2, has an alignment of antigen spots AS which does not match a grid to be employed later, which grid is used for assigning the spots AS to corresponding antigen types on the basis of their exact position, so that it is possible to carry out a detection of binding of antibodies of a liquid sample to particular antigen types by evaluation in a so-called second color channel.

FIG. 3A shows an exemplary embodiment of an antigen chip A in which antigen spots AS are arranged spaced apart on a substrate surface SO in antigen spot patterns AM, the antigen spots AS comprising an identical, common dye or first dye.

The antigen spots form respective antigen spot sets AG which, in turn, form respective regular antigen spot patterns AM. In this exemplary embodiment, these are patterns AM in which antigen spots are arranged running from top to bottom along a line.

The antigen chip A further has a reference pattern RM having reference spots which have a spot distance SD1 from one another.

The spot distance SD2 of the antigen spots of the antigen spot patterns AM is different from the spot distance SD1 of the reference pattern RM.

Here, the regularity parameter of the patterns RM, AM is the respective spot distance SD1, SD2 within the respective pattern RM or AM. Thus, the reference pattern RM differs from the antigen spot patterns AM with respect to the value of this regularity parameter or with respect to its regularity. The patterns RM, AM are arranged along an arrangement direction ANR. The patterns RM, AM each have a spreading direction ABR which is perpendicular to the arrangement direction ANR of the patterns AM, RM.

The spots of the patterns RM, AM comprise an identical, common dye.

It is assumed that the antigen spots of the antigen spot pattern AM1 comprise an identical, common antigen or an identical, common antigen type which differs from an antigen type or an antigen of the pattern AM2.

If such an antigen chip A having all its spots of the patterns RM, AM is incubated with a biological sample such as, for example, a blood serum, what can occur for the spots of the different antigen spot patterns AM1, AM2 owing to the different antigen types of the patterns AM1, AM2 are bindings of varying strength of antibodies from the biological, liquid sample to the respective antigen types.

Such binding is a so-called first antibody from the biological, liquid sample, and is then to be detected later.

Preferably, the antigen chip A has a further, second reference pattern RM2 which, with its reference spots, differs with respect to its regularity or its value of the regularity parameter both from the first reference pattern RM and from the antigen spot patterns AM. This is the case because the reference pattern RM2 has a spot distance SD3 which clearly differs from the spot distances SD1, SD2.

The common, identical dye of the spots of the patterns RM, RM2, AM is preferably visible in a first color channel as a red channel.

The regularity of the reference pattern RM differs from the antigen spot patterns AM and especially also from the second reference pattern RM2 by variation of a common regularity parameter of the patterns RM, AM and especially RM2. In the context of this application, a regularity can also be referred to as a periodicity of a pattern, the regularity parameter being a periodicity parameter. Differing spot patterns then have different values with respect to the same regularity parameter of the spot patterns.

FIGS. 5A and 5B respectively show a first image information item BI2 and a second information item BI2 having respective colors in different color channels due to respective dyes.

The first image information item BI1 shows an exemplary reference pattern RM and also an exemplary and preferably present second reference pattern RM2 in the first color channel owing to a color of the first dye. Furthermore, antigen spot patterns AM are visible in the first image information item BI1 owing to the color due to the first dye in the first color channel.

What is made possible by providing or using a proposed second reference pattern RM2 is that, in connection with automated image evaluation, an assumable sequence of antigen types in the arrangement direction ANR based on the individual antigen spot patterns AM can be corrected when the antigen chip A shown in FIG. 3A is rotated by 180°. Owing to the location of the first reference pattern RM and of the second reference pattern RM2 in relation to one another, it is then possible to detect such an undesired rotation of the antigen chip A in an image information item of the first color channel and to thus correct the location or the position of the antigen spot patterns along the assumed arrangement direction ANR even in the case of an undesired 180° rotation of the antigen chip.

The first dye is preferably a fluorescent dye. Alternatively, the first dye is a chromogenic substrate which, for the purpose of a chromogenic color, can form a bond with an enzyme which can be added by means of a further conjugate in connection with further incubation of an antigen chip. The color change due to binding of the chromogenic substrate with an enzyme can be considered to be a color-change product which is photometrically capturable.

The second image information item BI2 from FIG. 5B shows that a color in the second color channel due to the second dye is not significantly present for all antigen spot patterns AM. This is presumably the case because there was no substantial or significant binding of antibodies of the liquid, biological sample to the corresponding antigen types of the corresponding antigen spot patterns, meaning that, in the case of an incubation of the antigen chip with a second conjugate containing a second antibody having a label due to the second dye, the second antibodies were then not bound to first antibodies from the liquid biological sample.

The second dye is preferably a fluorescent dye.

Preferably, the second fluorescent dye is a chromogenic substrate which can bind to an enzyme, it being possible for the enzyme to be present in a conjugate which can be used for incubation of the spots in a further processing step. The enzyme then forms, with the chromogenic substrate, a color-change product which is photometrically capturable.

Preferably, the second dye is an enzyme, and so, in the case of an incubation of the spots with a conjugate comprising a chromogenic substrate, the enzyme forms a bond with the chromogenic substrate in order to generate a color-change product which is photometrically capturable.

Preferably, the second dye is an enzyme which, in connection with a further processing step, can form a bond or interaction as a result of incubation of the spots with a conjugate comprising a further substrate, so that radiation is emitted owing to a chemiluminesence reaction.

Preferably, the second dye is a substrate for a chemiluminescence reaction, and so, in the case of incubation of the spots with a conjugate comprising an enzyme which can in turn undergo a reaction with the substrate, the chemiluminescence reaction is elicited, with the result that chemiluminescence radiation is emitted.

If a dye is a fluorescent dye, it is, for example, possible to excite a fluorescence radiation FL by an excitation light AL1 or AL2, as shown in FIG. 6. The fluorescent light FL is preferably the light emitted by the first fluorescent dye. The axes in the illustration in FIG. 6 show the wavelength WL on the abscissa and the intensity IN on the ordinate.

The axes in the illustration in FIG. 7 show the wavelength WL on the abscissa and the intensity IN on the ordinate. In a graph having a wavelength WL on the abscissa and an intensity IN on the ordinate, FIG. 7 shows a spectrum of an excitation light AL, a spectrum FL1 of a first fluorescence radiation due to a first fluorescent dye and a spectrum FL2 of a second fluorescence radiation due to a second fluorescent dye.

The first fluorescence FL1 can encompass emission of light in a first wavelength range and the second fluorescence FL2 can encompass emission of light in a second wavelength range, the first wavelength range and the second wavelength range having only a slight or essentially no overlapping range, for instance an overlapping range or overlap that, for example, corresponds to less than 10%, especially less than 5%, of an integral of an emission of the first fluorescence over wavelength.

The first fluorescent dye can, for example, fluoresce in a red wavelength range, for example in a range between 550 nm and about 800 nm with a maximum between 600 nm and 660 nm. To this end, the first fluorescent dye can be the dye DY521XL for example. The excitation of the first fluorescent dye can occur in a frequency range of, for example, between 450 nm and 500 nm with a maximum of, for example, between 550 nm and 580 nm. The excitation of the second fluorescent dye can occur substantially in the same wavelength as the excitation of the first fluorescent dye. The second fluorescent dye can, for example, fluoresce in a green wavelength range, for example in a range between 500 nm and about 600 nm with a maximum between 510 nm and 530 nm. To this end, the second fluorescent dye can be the dye FITC for example.

What is thus required in a device for automated detection of antibodies in a sample is, for example, only a single illumination-light source for generating the excitation light that can be realized as a relatively narrow band. The excitation light can thus be advantageously filtered out before detection of the first fluorescence by a first camera and of the second fluorescence by a second camera or of both fluorescent signals by the first or the second camera (e.g., after a filter change) without substantial detection of interfering excitation light.

Coming back to FIG. 5A, it can be noted that preferably the reference spots of the reference spot set RM can comprise the dye in a dye concentration greater than the dye concentrations in which the antigen spots or the antigen spot sets or antigen spot patterns AM and especially also the reference pattern RM2 comprise the first dye or the identical, common dye. Preferably, the second reference pattern RM2 can also comprise said identical, common dye in a dye concentration greater than the dye concentrations in which the antigen spots of the antigen spot sets AM comprise the identical, common dye.

If the spots of the reference spot set RM—and especially also the second reference spot set RM2—were to comprise the identical, common dye in a higher dye concentration, this could facilitate detection of the reference pattern RM— and especially also the further reference pattern RM2—in connection with automated image processing, since the color intensities of said spots in an image information item would be greater than those of the antigen spots of the antigen spot sets.

Coming back to FIG. 3A, it can be further noted that the reference pattern RM forms a reference line pattern and that furthermore the antigen spot patterns AM likewise form reference line patterns, the lines of the patterns RM and AM having an identical spreading direction. The reference pattern RM2 likewise forms a reference line pattern. This is also to be referred to as further or second reference line pattern.

Within the line patterns RM, RM2, AM, the respectively associated spots of these patterns substantially follow one another at respectively regular, preferably substantially equidistant distances, the regular, preferably substantially equidistant distance of the reference spots of the reference line pattern RM differing from the regular, preferably substantially equidistant distances of the antigen spots of the antigen line patterns AM. If a further, second reference pattern RM2 is present as a line pattern besides the reference pattern RM, said pattern RM2 differs both from the first reference pattern RM and from the antigen line patterns AM in that the associated spots of the pattern RM2 differ, in terms of their regular, preferably substantially equidistant distance, from the regular, preferably substantially equidistant distances of the antigen spots of the antigen line patterns AM and of the spots of the first reference pattern RM.

FIG. 3B shows a preferred variant A2 of an antigen chip A2 according to the invention, in which only three antigen spot patterns AM1, AM2, AM3 are present on the antigen chip A2. This is a subset of patterns already present in this arrangement on the antigen chip A from FIG. 3A. Here too, the patterns RM, RM2, AM are arranged in an arrangement direction ANR. To illustrate one of the advantages of the method according to the invention and of the antigen chip according to the invention, it is assumed that what is striven for is to produce an antigen chip as shown in FIG. 3B.

FIG. 4A shows a substrate or a substrate surface SU. The substrate surface SU is preferably a surface of a glass substrate or of a glass substrate coated with a membrane and/or film. On the substrate SU, different patterns RM, RM2, AM are to be applied to the substrate along an arrangement direction ANR. To this end, the spots of the respective patterns RM, RM2, AM are applied to the substrate SU by means of respective pipettes P. Here, the pipettes P can be stationary, and so the pipettes P apply respective spots for a respective spot set to the substrate surface SU preferably as a line pattern by means of respective drops T, it being possible for the substrate SU to be shifted with respect to the pipettes P in a feed direction VR1 such that the abovementioned regular patterns are formed. Thus, the reference spots of the reference spot set RM form a reference line pattern and the antigen spots of the respective antigen spot sets AM form respective antigen line patterns. The same applies to the preferably present second reference pattern RM2.

If the substrate surface SU has been shifted with respect to the pipettes P in the feed direction VR1 such that the corresponding line patterns RM, RM2, AM have formed, the result is a distance DI1 which specifies, in the arrangement direction of the patterns ANR, the minimum width of the antigen chip to be produced. If the substrate support SU is then driven back against the feed direction VR1 into the original position depicted in FIG. 4A, it is then possible by a movement or feeding of the substrate support SU in the feed direction VR2 by the distance DI1 to form in turn a new set of corresponding reference patterns RM, RM2 and antigen spot patterns AM, the substrate support SU then simply being fed in turn in the feed direction VR1 as well in order to bring about a relative movement of the substrate support SU with respect to the pipettes P. To form the corresponding line patterns RM, RM2, AM having different regular distances of their respective spots, the corresponding pipettes P must thus only be controlled in such a way that the drops T are formed at different frequencies or different distances along the feed direction VR1. Formation of the patterns RM, RM2, AM as line patterns allows a particularly effective production of the antigen chip according to the invention. Thus, on the substrate support SU, it is then possible to generate patterns for multiple antigen chips in serial processing, and it is not necessary to use a distinct substrate support SU for each antigen chip. Application by the pipette heads is achieved especially by a so-called piezo pressure by means of a piezoelectric microdispenser as a particular embodiment of the pipettes P. It can thus be stated that application of reference spots and antigen spots to the level substrate surface SU is realized in such a way that an antigen chip according to the above-described embodiment results.

FIG. 4B now illustrates a particular advantage of the antigen chip according to the invention. It would be possible to exactly fragment the substrate surface from FIG. 4A in such a way that the substrate SU is always exactly fragmented according to the distance DI1 in parallel to the spreading direction of the patterns, i.e., perpendicularly to the arrangement direction ANR of the patterns. The result would then be a location of the reference pattern RM and of the antigen spot patterns AM on the various antigen chips to be thus produced at always the same, recurring site or position on the corresponding antigen chip. However, owing to the formation of the antigen spot patterns AM and of the reference pattern RM and especially of the second reference pattern RM2 that is according to the invention, it is possible, as illustrated in FIG. 4B, to perform such fragmentation at at least one, especially at two sites, of the substrate SU at a distance DI2 to be chosen only approximately, with the result that corresponding antigen chips A11 and A12 from FIG. 4B can arise. What is essential is that the distance DI2, according to which the substrate support SU is fragmented, is at least just as great as the distance DI1 or else greater than said distance DI1. The distance DI2 to be chosen must furthermore merely be smaller than twice the distance DI1 in order to avoid a complete repetition of the entirety of all patterns AM, RM, RM2. Although what then results on the resultant antigen chip A11 in the right-hand region is a repetition of the antigen spot pattern AM1, the sequence of the corresponding antigen types of the antigen spot patterns AM1, AM2, AM3 can, owing to the distinguishability of said patterns with respect to the reference pattern RM and especially the reference pattern RM2, be used in connection with automated image evaluation for detecting binding of antibodies for at least each antigen type or each of the antigen spot patterns AM1, AM2, AM3. The subsequent antigen chip A12 produced has, owing to the choice of fragmentation distance DI2 over the repetition distance DI1 of the antigen spot patterns and of the reference pattern and especially of the second reference pattern, then at least each type of an antigen spot pattern AM1, AM2, AM3 and the reference pattern RM and especially also the second reference pattern RM2 at least once. Only through the formation of the antigen spot patterns and also the at least one reference pattern RM that is according to the invention does the possibility arise of not having to perform the fragmentation of the substrate SU at fixed positions, as specified by the distance DI1; instead, this distance of fragmentation sites can be chosen distinctly more freely or inexactly. In the solution according to the prior art, it is necessary, as elucidated above with reference to FIGS. 2 and 1, that a respective antigen spot ASX occur on a corresponding substrate or within a corresponding pattern at a very exact, corresponding position in order to be able to correctly perform an assignment of the spot ASX to a particular antigen type. This requirement is circumvented in a particularly skilful manner by the antigen chip according to the invention and the proposed method for automated detection of antibodies and the proposed method for automated image processing, and leads to a particularly simple way of producing antigen chips A11, A12.

Furthermore, the reference spots RM of the reference pattern can likewise additionally preferably comprise an antigen, with the result that it is then possible to detect binding of antibodies of the biological sample, to which second antibodies of a conjugate labeled with a second dye can bind in turn, and it is thus possible to use a further, additional antigen type with respect to detection of antibodies in the biological sample.

Preferably, the reference spots of the reference pattern RM and especially of the reference pattern RM2 comprise antibodies, especially in the form of anti-human IgG. Such an antibody can then form a bond with an antibody of a liquid patient sample, for example a blood serum, and so, after further incubation of the reference spots with a conjugate which can in turn comprise a second antibody labeled with a second dye, there is binding of the second dye to the reference spots. As a result, it is then possible to check later in connection with automated image processing and with a method for detection of antibodies whether the antigen chip was correctly incubated with the sample and/or the conjugate. The reference spots RM, RM2 can thus be used as an incubation control.

FIG. 13 show again steps of the proposed production method. In step S100, what takes place is provision of a substrate having a level substrate surface. In step S101, what takes place is application of reference spots to the level substrate surface. In a step S102, what takes place is application of antigen spots to the level substrate surface. What takes place here is the application of the antigen spots and the reference spots to obtain an antigen chip in accordance with one embodiment in the manner described above. In a preferably performable step S103, what takes place is fragmentation of the substrate in order to obtain multiple antigen chips. The fragmentation takes place with observance of a distance between two fragmentation sites that, in the case of a repetitive sequence of antigen spot patterns and reference spot patterns, is at least just as great as a distance describing said repetitive sequence in an arrangement direction of the patterns.

If multiple antigen chips were produced in the manner described above, multiple antigen chips can be provided combined on one slide. In relation to this, FIG. 18 shows a slide OT which, on different fields FE, comprises multiple antigen chips A in each case.

In relation to this, FIG. 19 shows a detailed representation of an individual field FE comprising multiple antigen chips A.

As depicted in FIGS. 3A, 3B, 4A, and 4B, the antigen spot patterns AM and the reference pattern RM can differ in that they have a respective different periodicity or a different regular distance of antigen spots in relation to one another. This design of the antigen spot patterns AM and of the reference pattern RM is illustrated in this manner here only by way of example. Preferably, the reference pattern RM, especially also the second reference pattern RM2, differs from the antigen spot patterns AM in that, along the arrangement direction ANR, the reference pattern RM has, in relation to a next immediately adjacent pattern, such an immediate neighboring distance which differs from the other neighboring distances of the antigen spot patterns AM. Here, the patterns RM, AM thus need not have different regular distances of their respective spots within the patterns RM, AM, but can differ on the basis of a distance or a neighboring distance toward the next pattern in or along the arrangement direction ANR.

Furthermore, it is possible that the reference pattern RM, and especially also the second reference pattern RM2, comprises such spots which have an identical size, the size of the spots of the reference pattern RM differing from the sizes of the antigen spots of the antigen spot patterns AM. Here, the reference pattern RM and the antigen spot patterns AM can thus differ in that spots of different size are respectively formed for the different respective patterns RM, AM, which, in connection with a production method as illustrated in FIG. 4A, can be used, for example, by different pipette sizes for generation of different sizes of spots or different sizes of drops for formation of the spots.

FIG. 10 shows preferred steps of a method according to the invention for automated detection of antibodies in a liquid biological sample.

In a step S1, what takes place is provision of an antigen chip in accordance with any of the above-described embodiments. In a step S2, what takes place is incubation of the spots of the antigen chip with the biological sample. In a step S3, what takes place is incubation of the spots with a conjugate which comprises a secondary antibody labeled with a second dye. In a step S4, what takes place is provision or acquisition of a first image information item BI1, BI11 which represents a color of reference spots and of antigen spots of the antigen chip due to a first dye.

If the first dye is a fluorescent dye, what preferably takes place in step S4 is illumination of the antigen chip with a first excitation light of a first wavelength for excitation of an emission of first fluorescence radiation due to the first dye. The first image information item then represents a color of the reference spots and of the antigen spots of the antigen chip due to the first fluorescence radiation. This preferably takes place in a so-called red channel.

In a step S5, what takes place is detection of the reference pattern and an associated reference position on the substrate surface assuming an arrangement direction of the patterns on the substrate surface on the basis of the at least one first image information item. The reference position can be provided as a reference position information item RPI.

In a step S6, what takes place is detection of the respective antigen spot patterns and the respective associated further positions on the substrate surface assuming an arrangement direction of the patterns on the substrate surface on the basis of the at least one first image information item. This can be provided as a so-called further, overall position information item AGMPI based on the further positions of the antigen spot patterns.

In a step S7, what then takes place is generation of an assignment information item ZI, which indicates an assignment of the respective antigen spot patterns to the respective antigen types, on the basis of the detected reference position and the detected further positions.

In a step S8, what then takes place is acquisition or provision of a second image information item BI2, BI12 which represents a potential color of the antigen spots and preferably also the reference spots due to the second dye. In connection with said step S8, what preferably takes place if the second dye is a fluorescent dye is illumination of the antigen chip with a second excitation light of a second wavelength in order to excite an emission of second fluorescence radiation. Preferably, the second excitation light of the second wavelength is, in terms of its wavelength range, identical to the wavelength range of the first excitation light for excitation of the first fluorescence radiation of the first fluorescent dye. The second image information item then preferably represents a potential color of the antigen spots of the antigen chip due to the second fluorescence radiation.

In a step S9, what can then take place, preferably using the reference position information item RPI and the further position information item AGMPI, is determination of respective measures of binding which indicate respective bindings or degrees of binding of antibodies of the biological sample to respective antigen types, on the basis of the second image information item BI2, BI12 and the assignment information item ZI.

Said measures of binding can be preferably output in a method step S10, preferably in the form of a data element BD via a data interface.

Steps S4 to S9 can be preferably carried out in the method according to the invention for automated image processing for detection of antibodies in a liquid biological sample in accordance with one embodiment. The same applies to step S10, which is to be preferably carried out.

Thus, in step S10, what preferably takes place is provision, via a data interface, of an information item which indicates the position of the patterns and preferably also the position of individual antigen spots and individual reference spots on the antigen chip.

The assignment of antigen spot patterns to respective antigen types that is carried out in step S7 is preferably carried out in a manner as illustrated in FIG. 11B. In this case, a spatial sequence of the reference position of the reference pattern and of the respective further positions of the respective further antigen spot patterns is determined in a step S71. This position can also be referred to as positions along an arrangement direction, especially assumed arrangement direction, of the patterns on the substrate surface.

In a step S72, what takes place is provision of a sequence data set ADS which indicates a sequence of antigen types. This is especially a spatial sequence of antigen types along an arrangement direction of patterns.

FIG. 11C illustrates an exemplary sequence data set ADS which, for a sequence of patterns along an arrangement direction ANR, indicates that for consecutive positions in corresponding fields PN there are respective corresponding antigen types AT1, AT2, AT3 in corresponding fields AT. The sequence data set ADS thus indicates a spatial sequence of respective antigen types for respective positions along an arrangement direction ANR of spot patterns. Furthermore, for particular positions, corresponding reference pattern types R1, R2 in corresponding fields RT are also specified. In this preferred exemplary embodiment, a first and a second reference pattern are present. A person skilled in the art understands that, in the case of only one reference pattern, only one reference pattern type R1 is present.

In a substep S73 from FIG. 11B, what then takes place is generation of an assignment information item ZI which indicates the assignment of the respective antigen spot patterns to the respective antigen types. This is done on the basis of the detected reference position, the detected, respective further positions of the respective antigen spot patterns, and the sequence data set ADS.

Preferably, a further reference position of a second reference pattern is also detected in connection with the method and taken into account in connection with the assignment of the respective antigen spot patterns to the respective antigen types. This makes it possible to compensate for or take into account an undesired 180° rotation of the antigen chip.

In relation to this, FIG. 11A shows steps to be preferably carried out. Following the above-described step S5, what then takes place in a step S5A is detection of the second reference pattern and an associated second reference position on the basis of the first image information item. What then follows is the above-described step S6. In a subsequent step S7A, what then takes place is the generation of the assignment information item ZI which indicates the assignment of the respective antigen spot patterns to the respective antigen types. This is done on the basis of the detected first reference position, the detected second reference position and the detected further positions of the respective antigen spot patterns and also preferably the sequence data set.

FIG. 20A shows a first reference pattern RM, a second reference pattern RM2 and antigen spot patterns AM represented by a first image information item BI11 in a first color channel, which is preferably a red channel.

In relation to this, FIG. 20B shows corresponding exemplary antigen spot positions AGSPI1, which are drawn in as rectangles, in the first image information item BI11. After detection of such antigen spot positions AGSPI1 and corresponding positions for the reference patterns RM, RM2 from FIG. 20A, it is then possible to assign the individual spots to individual patterns AM, RM, RM2, especially line patterns.

For respective patterns AM, RM, RM2, it is thus possible to determine respective positions along the arrangement direction ANR. It is then simply possible to assign individual antigen spot patterns to individual antigen types in the manner described above, preferably on the basis of a sequence data set.

FIG. 21A shows a color of spots due to a second dye of the same antigen chip as from FIGS. 20A and 20B. FIG. 21A shows a second image information item BI12 which represents a color of spots, especially of the antigen spots due to the second dye and thus in a second color channel, preferably a green channel.

Here, the positions of the spots that were identified on the basis of the first image information item BI11 from FIG. 20B can be used in order, as shown in FIG. 21B, to determine in the second image information item BI21 whether bindings of particular antibodies from the biological sample are present for particular antigen spots and thus for particular antigen types. On the basis of this determination or evaluation, it is then possible to determine and preferably subsequently provide measures of binding for respective antigen types.

In connection with method steps S5 and S6 mentioned above in relation to FIG. 10, it is possible to carry out preferred submethod steps as drawn in in FIG. 14. In a method step S20, what then takes place is identification of multiple potential patterns on the basis of the at least one first image information item. In a further method step S21, what then takes place is detection of respective regular mean spot distances of spots within a respectively identified pattern for the respectively identified, potential pattern. In a step S22, what then takes place is selection of one of the identified patterns as the reference pattern on the basis of the detected mean spot distances. As is apparent to a person skilled in the art, this can also be carried out for the second reference pattern.

There now follows an explanation of how identification of individual spots and then identification of patterns and assignment of spots to patterns can be achieved in detail. In relation to this, FIG. 15 shows steps to be preferably carried out.

Using the first image information item BI11 from FIG. 20A or on the basis thereof, what takes place first in a step S30 is identification of circular objects in the first image BI11 by means of a Hough transform.

In a step S31, what takes place for each circle found is extraction of properties for the identified circular objects such as, for example, a contour and/or intensity properties. The properties can be a circumference of a circle, a deviation from a perfect free circle or the average intensity of an object.

In a step S32, what then takes place, using a support vector machine, is classification of the proposed circular objects from the Hough transform with the properties thereof into a first class "spot" or a second class "image artifact". Only those image regions or objects which are classified as a spot are subsequently used.

For every image region classified as a spot, it is then possible to determine or to have determined already in step S31 a position on the antigen chip or in the image information BI11 in terms of the X and Y position. In a step S33, what then takes place is combination of spots to form a pattern or a line pattern or a line. Here, what is generated is a list of the spots sorted on the basis of their Y position in the image. Thereafter, a spot is taken from the list and its next neighbour in Euclidean distance is ascertained. If both spots are at an angle of approx. 90° to one another or form a straight line which forms an angle of 90° with respect to the arrangement direction, it is assumed that they belong to the same pattern or the same line. This value of 90° can also be provided with a window of uncertainty of plus or minus several degrees. If such an association of the two contemplated spots with one another to form a pattern or to form such a straight line of approx. 90° in relation to the arrangement direction of the patterns is not present, the next spot from the list, sorted according to distance or Y position, is contemplated. If no more spots from the list can be assigned to the currently contemplated pattern or the currently contemplated line, a new pattern or a new line in a direction perpendicular to the arrangement direction of the patterns is started. By means of such a method, the spots are then assigned to respective patterns or respective lines in an iterative manner.

In a step S34, what then takes place is consecutive numbering of the patterns or line patterns. This is preferably done such that the pattern or the line, the spots of which have the greatest mean distance from one another, is respectively assumed to be the reference pattern or the reference line pattern. Preferably, a second reference pattern is assumed to be that pattern or that line in which the spots have the smallest mean distance from one another.

In a step S35, it is then possible, on the basis of the second image information item BI12 from FIG. 21B, to ascertain, for those spots assigned to a pattern or a line, the respective intensities or pixel intensities per spot in the second color channel on the basis of a color due to the second dye. This is preferably done as the median value of the intensities of a spot.

Finally, what can then take place in a step S36 is determination of a average intensity value of a pattern such that the median value of the median intensities of the spots of a pattern is ascertained. Said median value is then a measure of binding which indicates binding or a degree of binding of antibodies from the biological sample to a particular antigen type.

It is thus preferably possible to use, in connection with step S9 for determining the measures of binding on the basis of the second image information item BI12, the antigen spot position information item AGSPI obtained beforehand from step S6 on the basis of the first image information item BI11 and also the reference spot position information item RSPI obtained in step S5, as depicted in FIG. 16. The detection of a reference spot pattern and the respective antigen spot patterns thus includes detection of individual spot positions and assignment of spots or spot positions to the reference pattern and the respective antigen spot patterns.

Preferably, a measure of binding is determined by using a threshold value which is provided via a data element and which can be applied to the median intensity ascertained for a pattern or an antigen type. If the median intensity value of a pattern falls short of the threshold value, it is assumed that there is no binding of antibodies at all. A value indicating that there is binding of antibodies to the corresponding antigen type is output only if the median value of a pattern exceeds the specified threshold value.

The measures of binding can be output via a data element in which, as drawn in in FIG. 12, a data set BD indicates an assignment of measures of binding BM to corresponding antigen types AT. The data set BD can, for example, be a list. For an antigen type AT1, a measure of binding BM1 is then present, as are corresponding measures of binding BM2, BM3 for corresponding antigen types AT2, AT3.

As described above, in an alternative embodiment, the reference pattern has, in relation to an immediately adjacent pattern along the arrangement direction of the patterns, such a neighboring distance which differs from the other neighboring distances of the antigen spot patterns. In relation to this, FIG. 22A shows an embodiment A21 in which only one reference pattern RM is present. The reference pattern RM has a neighboring distance DI11 in relation to the next directly adjacent pattern AM1 in the arrangement direction ANR that is greater than the neighboring distance DI12 of the other patterns AM1, AM2, AM3 in relation to their next directly adjacent patterns AM2, AM3, RM in the arrangement direction ANR.

In this embodiment, it is then possible to preferably carry out the following steps in connection with the method for automated detection and the method for automated image processing:

identifying multiple patterns AM1, AM2, AM3, RM on the basis of the first image information item;

detecting respective neighboring distances DI11, DI12 of the identified patterns, especially along the arrangement direction of the patterns, in relation to their respectively next patterns adjacent, especially directly or immediately, in the direction of the arrangement direction of the patterns;

selecting one of the identified patterns as the reference pattern on the basis of the detected neighboring distances DI11, DI12.

Here, it is possible to use the spot positions of the reference spots and of the antigen spots that were detected, as shown in FIG. 20B, on the basis of the first image information item BI11 in order, as described above in detail, to assign the spots to respective patterns or line patterns, with the result that multiple patterns are simply identified on the basis of the first image information item BI11. Along or in the arrangement direction ANR of the patterns, it is then possible to determine respective neighboring distances DI11, DI12 between the patterns, i.e., for example a neighboring distance for the reference pattern in relation to the next pattern which is to the right thereof and directly adjacent in the direction of the arrangement direction ANR. If the reference pattern has a neighboring distance which differs from the neighboring distances of the antigen spot patterns, the reference pattern can be detected and identified with certainty.

As described above, what is provided in an alternative embodiment is that, within the reference pattern and within the antigen spot patterns, the respectively associated spots have a respective, identical size, wherein the size of the reference spots of the reference pattern differs from the sizes of the antigen spots of the antigen spot patterns. In relation to this, FIG. 22B shows a preferred embodiment A22 of an antigen chip in which only one reference pattern RM is present. The reference spots of the reference pattern RM have an identical size. Said size differs from the identical, common size which the antigen spots of the antigen patterns AM have.

In this embodiment, it is then possible to preferably carry out the following steps in connection with the method for automated detection and the method for automated image processing:

identifying multiple patterns RM, AM1, AM2, AM3 on the basis of the at least one first image information item, detecting respective spot sizes for the respective identified patterns RM, AM1, AM2, AM3;

selecting one of the identified patterns as the reference pattern RM on the basis of the detected spot sizes Here, it is possible to use the spot positions of the reference spots and of the antigen spots that were detected, as shown in FIG. 20B, on the basis of the first image information item BI11 in order, as described above in detail, to assign the spots to respective patterns or line patterns, with the result that multiple patterns are simply identified on the basis of the first image information item BI11. For each spot, a property such as the circumference of the identified circle or circular object is then determined. As a result, spots of identical circumference or identical size can then be assigned to the same pattern. That pattern, the spots of which have on average the largest spot size compared to the other patterns, can then be detected as the reference pattern.

FIG. 8 shows a device V1 according to the invention in accordance with one embodiment for automated detection of antibodies in a sample. The device V1 comprises a so-called microscope device.

An antigen chip C can be viewed through an objective O by means of at least one camera K1, K2.

The cameras K1, K2 can be referred to as image acquisition units. The assembly from FIG. 8 for the device V1 provides an explicit separation of two color channels or optical channels before acquisition of image information items by separate image acquisition units K1, K2. It is obvious to a person skilled in the art that such a device can also be realized by a temporal exchange of optical filters, in that only a single image acquisition unit is provided, but the use of the different optical filters for different color channels makes it possible to acquire the above-described respective image information items of the respective color channels.

A fluorescence light source LQ emits an excitation light AL which is filtered by means of an excitation light filter F1 such that an excitation light spectrum AL, as described in FIG. 7, is directed onto the dichroic mirror SP1. The dichroic mirror SP1 then directs said excitation light AL toward the objective O, through which the excitation light then strikes the antigen chip C and the spots thereof. First and second fluorescence radiation emitted by the antigen chip C or the fluorescent dyes of the spots then travel, by means of the objective O, through the dichroic mirror SP1 toward an optical filter F2 which blocks the excitation light AL or the spectrum thereof and transmits the fluorescence radiation of the first color channel and also of a second color channel. The fluorescence radiation then reaches a further dichroic mirror SP2 which reflects fluorescence radiation of the first color channel or first fluorescence radiation toward a first image acquisition unit or camera K1. Preferably, filtering of the first fluorescence radiation from the incoming spectrum is additionally carried out by an optical filter FR. The filter FR is especially a red-channel filter.

The dichroic mirror SP2 transmits the second fluorescence radiation or light of the second color channel toward a second image acquisition unit or camera K2. Preferably, said radiation is filtered once more by a further optical filter FG, the optical filter FG being especially a green-channel filter.

The first camera K1 then acquires the first image information item BI1 and makes it available to the computing unit R. The second image acquisition unit K2 then acquires the second image information item BI2 and makes it available to the computing unit R2.

The first image acquisition unit and the second image acquisition unit as an example of at least one image acquisition unit are then thus designed for acquiring a first image information item BI1 which represents a color of reference spots and of antigen spots of an antigen chip C due to a first dye, especially a first fluorescent dye. Furthermore, the at least one image acquisition unit K1, K2 is designed for acquiring a second image information item BI2 which represents a potential color of the antigen spots of the antigen chip due to a second dye, especially a second fluorescent dye, after incubation of the antigen chip with the biological sample and with a conjugate which comprises a secondary antibody labeled with the second dye.

The computing unit R is especially designed to carry out one or more of steps S4, S5, S6, S7 and S9 from FIG. 10 that are described above in relation to the method for automated detection of antibodies and the method of automated image processing for detection of antibodies. To this end, the computing unit R appropriately controls the image acquisition units K1, K2 and the fluorescence light source LQ.

Furthermore, the device V1 from FIG. 8 preferably comprises a data interface DS1 via which data elements DA can be received or transmitted. In particular, it is possible here to transmit measures of binding via such data elements DA and to preferably receive data elements which indicate a threshold value.

The device V1 can exchange data elements DA via the data interface DS1. Such data elements DA can then be one or more of the following data elements:
- a threshold-value data element TH to be received, from FIG. 17,
- a sequence data set ADS to be received, from FIG. 11C,
- a binding data set BD to be output or provided, from FIG. 10,
- an assignment information item ZI to be output or provided, from FIG. 11A.

With the fluorescence light source LQ, the device V1 thus comprises an illumination unit for emitting excitation light for exciting an emission of first fluorescence radiation of a first wavelength range due to the first dye. Furthermore, the light source LQ is also at least one illumination unit for emitting excitation light for exciting an emission of second fluorescence radiation of a second wavelength range due to the second dye.

FIG. 17 shows preferred steps in connection with the described method for automated detection of antibodies and/or the method for automated image processing.

In a step S40, what takes place is, as described above, identification of antigen spots in the second color channel or the second image information item BI2 from FIGS. 21A and 21B using the antigen spot position information items AGSPI or the further position information item AGMPI. Furthermore, what preferably takes place if the reference spots also comprise an antigen is identification of the reference spots using the reference position information items RPI or the reference spot position information item RSPI.

In step S41, what takes place, in the manner described above, is assignment of image regions or spots to particular patterns and thus also to particular antigen types.

In a step S42, what takes place is determination of an average intensity or median intensity of a pattern in the second color channel or on the basis of the second image information item.

In method step S43, what takes place is providing or receiving a data set TH which indicates a threshold value to be applied to median intensities.

What then takes place in step S43 is application of said threshold value to the ascertained average intensities of the respective patterns.

In a step S44, what then takes place is determination of respective measures of binding for the respective patterns.

In a step S44a to be preferably carried out, what then takes place is output of a note to the user, preferably by means of an optical display unit or preferably by means of a data element to be output via a data interface, if the reference spots of the reference pattern in the second color channel or the second image information item do not have sufficient color or average intensity. This is done especially if the reference spots of the reference pattern comprise an antibody, especially IgG, by means of which it is possible to check whether a proper incubation of the antigen chip with a liquid biological sample of a human patient was carried out.

In step S45, what then takes place is the output of the measures of binding.

FIG. 9 shows one embodiment of a data network device V2 according to the invention, which can preferably also be referred to as a cloud system.

The data network device V2 for automated image evaluation for detection of antibodies in a liquid and biological sample comprises at least one data interface DS via which data elements DA2 can be exchanged via a data network.

The device V2 comprises at least one computing unit R2, which is preferably connected to the data interface DS via a data bus DB. Preferably, the data network device V2 comprises at least one storage unit MEM.

The at least one data interface DS is designed for receiving a first image information item which represents a color of reference spots and of antigen spots of an antigen chip due to a first dye. The at least one data interface DS is furthermore designed for receiving a second image information item which represents a potential color of the antigen spots of the antigen chip due to a second dye after incubation of the antigen chip with the biological sample and a conjugate which comprises a secondary antibody labeled with the second dye.

The computing unit R2 is designed to carry out the steps described above in relation to the method for automated image processing, especially one or more of steps S4, S5, S6, S7 and S9. Furthermore, the computing unit R2 is designed to carry out further steps of the method for automated image processing that are to be preferably carried out and that were explained in detail above.

The device V2 from FIG. 9 is furthermore preferably designed to provide, via the data interface DS, data elements DA2 which are an information item indicating the respective measures of binding of antibodies to the respective antigen types.

Furthermore, the data interface DS is further designed to indicate, via data elements, detected positions of antigen spots and/or patterns and reference spots or reference patterns.

In a method carried out by the device V2 from FIG. 9, what takes place is automated image processing for detection of antibodies in a liquid biological sample, especially by the first image information item being received via the at least one data interface DS and being provided by means of the at least one storage unit MEM, the second image information item furthermore being received via the data interface DS and being likewise provided by means of the storage unit MEM.

Preferably, the device V2 is designed to receive, via the data interface DS, a data element which indicates particular antigen types, in relation to which measures of binding are to be output. What then preferably takes place is an evaluation for said indicated particular antigen types and also transmission of a data element which indicates measures of binding of the corresponding particular antigen types.

Although some aspects have been described in connection with a device, it is evident that said aspects are also a description of the corresponding methods, and so a block or a component of a device can also be understood as a corresponding method step or as a feature of a method step. By analogy, aspects which have described in connection with a method step or as a method step are also a description of a corresponding block or detail or feature of a corresponding device.

Depending on particular implementation requirements, exemplary embodiments of the invention can realize the computing unit R, R2 in hardware form and/or in software form. Here, realization of a presently mentioned computing unit R, R2 can be achieved as at least one computing unit or else by an association of multiple computing units. Implementation can be achieved using a digital storage medium, for example a floppy disk, a DVD, a Blu-Ray Disc, a CD, a ROM, a PROM, an EPROM, an EEPROM or a FLASH memory, a hard disk or some other magnetic or optical memory, which stores electronically readable control signals which cooperate or can cooperate with a programmable hardware component such that the method in question is carried out.

A programmable hardware component can be formed as a computing unit by a processor, a central processing unit (CPU), a computer, a computer system, an application-specific integrated circuit (ASIC), an integrated circuit (IC), a system on a chip (SOC), a programmable logic element or a field-programmable gate array with a microprocessor (FPGA).

The digital storage medium can therefore be machine-readable or computer-readable. Some exemplary embodiments thus comprise a data carrier having electronically readable control signals capable of cooperating with a programmable computer system or a programmable hardware component such that one of the methods described herein is carried out.

In general, exemplary embodiments or parts of exemplary embodiments of the present invention can be implemented as a program, firmware, computer program or computer program product containing a program code or as data, the program code or the data being effective in carrying out one of the methods or part of a method when the program runs on a processor or a programmable hardware component.

The invention claimed is:

1. An antigen chip, comprising:
a level substrate surface with antigen spots applied thereon, wherein the antigen spots are spaced apart and comprise an identical, common dye,
wherein the antigen spots form respective antigen spot sets, wherein the antigen spot sets form corresponding respective, regular antigen spot patterns,
wherein the antigen spots of a same antigen spot set comprise an identical, common antigen type, and wherein two or more of the antigen spot sets comprise different antigen types,
wherein reference spots are applied on the level substrate surface, wherein the reference spots form a reference spot set, wherein the reference spot set forms a reference pattern having a regularity, wherein the regularity of the reference pattern differs from a regularity of the antigen spot patterns, and
wherein the reference spots comprise the identical, common dye.

2. The antigen chip as claimed in claim 1, wherein the regularity of the reference pattern differs from regularity of the antigen spot patterns by one or more of the following criteria:
within the reference pattern and within the antigen spot patterns, the reference spots and the antigen spots follow one another at respective regular distances, wherein a regular distance of the reference spots of the reference pattern differs from a regular distance of the antigen spots of the antigen spot patterns;
the reference pattern has, in relation to an immediately adjacent antigen spot pattern, a neighboring distance which differs from other neighboring distances of the antigen spot patterns; and/or
within the reference pattern and within the antigen spot patterns, the reference spots and the antigen spots have a respective, identical size, such that a size of the reference spots of the reference pattern differs from a size of the antigen spots of the antigen spot patterns.

3. The antigen chip as claimed in claim 1,
wherein the reference pattern and the antigen patterns are arranged along an arrangement direction,
and wherein the reference pattern and the antigen patterns have respective spreading directions, wherein the respective spreading directions run substantially perpendicularly to the arrangement direction.

4. The antigen chip as claimed in claim 1,
wherein the reference spots of the reference spot set form a reference line pattern, and wherein the antigen spots of the respective antigen spot sets form respective antigen line patterns, and
wherein the reference line pattern and antigen line patterns run substantially parallel to one another.

5. The antigen chip as claimed in claim 1,
wherein the reference spots comprise first reference spots, wherein the first reference spots form a first reference spot set, wherein the first reference spot set forms a first regular reference pattern,
wherein the reference spots comprise second reference spots, wherein the second reference spots form a second reference spot set, wherein the second reference spot set forms a second regular reference pattern,
wherein the second reference spots comprise the identical, common dye, and
wherein regularity of the second regular reference pattern differs from regularity of the antigen spot patterns of the antigen spot sets, and from regularity of the first regular reference pattern of the first reference spots.

6. The antigen chip as claimed in claim 1, wherein the reference spots further comprise an antigen.

7. The antigen chip as claimed in claim 1, wherein the reference spots further comprise an antibody.

8. A method for automated detection of antibodies in a liquid biological sample by means of an antigen chip, the method comprising:
providing the antigen chip as claimed in claim 1,
incubating the reference spots and the antigen spots of the antigen chip with the biological sample,
incubating the reference spots and the antigen spots with a conjugate, wherein the conjugate comprises a secondary antibody labeled with a second dye,
acquiring or providing at least one first image information item, wherein the at least one first image information item represents a color of the reference spots and of the antigen spots due to a first dye, detecting the reference pattern and an associated reference position on the basis of the at least one first image information item, detecting the respective antigen spot patterns and respective associated further positions on the basis of the at least one first image information item, generating an assignment information item, wherein the assignment information item indicates an assignment of the respective antigen spot patterns to respective antigen types, on the basis of detecting the associated reference position and the respective associated further positions, acquiring or providing a second image information item, wherein the second image information item represents a potential color of the antigen spots due to the second dye, and determining respective measures of binding, wherein the respective measures of binding indicate respective bindings of antibodies of the biological sample to the respective antigen types, on the basis of the second image information item and the assignment information item.

9. A method for automated image processing for detection of antibodies in a liquid biological sample, the method comprising:

providing or acquiring at least one first image information item, wherein the at least one first image information item represents a color of the reference spots and of the antigen spots of the antigen chip as claimed in claim 1 due to a first dye, detecting the reference pattern and an associated reference position, detecting the respective antigen spot patterns and respective associated further positions, on the basis of the at least one first image information item, generating an assignment information item, wherein the assignment information item indicates an assignment of the respective antigen spot patterns to respective antigen types, on the basis of detecting the associated reference position and the respective associated further positions, providing or acquiring a second image information item, wherein the second information item represents a potential color of the antigen spots of the antigen chip due to a second dye after incubation of the reference spots and the antigen spots of the antigen chip with the biological sample and with a conjugate, wherein the conjugate comprises a secondary antibody labeled with the second dye, and determining respective measures of binding, wherein the respective measures of binding indicate respective bindings of antibodies of the biological sample to the respective antigen types on the basis of the second image information item.

10. The method as claimed in claim 8, wherein the associated reference position is an associated first reference position, the method further comprising:

detecting a second regular reference pattern and an associated second reference position on the basis of the first image information item, and generating the assignment information item wherein the antigen chip comprises the reference spots, wherein the reference spots comprise first reference spots, wherein the first reference spots form a first reference spot set, wherein the first reference spot set forms a first regular reference pattern, wherein the reference spots comprise second reference spots, wherein the second reference spots form a second reference spot set, wherein the second reference spot set forms the second regular reference pattern, wherein the second reference spots comprise the identical, common dye, and wherein regularity of the second regular reference pattern differs from regularity of the antigen spot patterns of the antigen spot sets, and from regularity of the first regular reference pattern of the first reference spots.

11. The method as claimed in claim 8, wherein the assignment of the respective antigen spot patterns to respective antigen types is achieved by determining a spatial sequence of the associated reference position and of the respective associated further positions, providing a sequence data set which indicates a sequence of antigen types, and generating the assignment information item, wherein the assignment information item indicates the assignment of the respective antigen spot patterns to respective antigen types, on the basis of detecting the associated reference position and the respective associated further positions, and the sequence data set.

12. A method for producing an antigen chip for immunodiagnostics, the method comprising:

providing a substrate having a level substrate surface, applying reference spots to the level substrate surface, and applying antigen spots to the level substrate surface, wherein application of the reference spots and of the antigen spots is carried out such that the reference spots and the antigen spots of the antigen chip are configured as per the antigen chip as claimed in claim 1.

13. The method as claimed in claim 12, further comprising: fragmenting the substrate in order to obtain multiple antigen chips.

14. The method as claimed in claim 12, wherein the level substrate surface is a surface of a glass substrate or of a glass substrate coated with a membrane and/or film.

15. A device for automated image processing for detection of antibodies in a liquid biological sample, comprising:

at least one image acquisition unit configured to acquire at least one first image information item, wherein the at least one first image information item represents a color of the reference spots and of the antigen spots of the antigen chip as claimed in claim 1 due to a first dye, and acquire a second image information item, wherein the second information item represents a potential color of the antigen spots of the antigen chip as claimed in claim 1 due to a second dye, after incubation of the reference spots and the antigen spots of the antigen chip with the biological sample and with a conjugate, wherein the conjugate comprises a secondary antibody labeled with the second dye, and at least one computing unit configured to detect the reference pattern and an associated reference position, on the basis of the at least one first image information item, detect the respective antigen spot patterns and respective associated further positions, on the basis of the at least one first image information item, generate an assignment information item, wherein the assignment information item indicates an assignment of the respective antigen spot patterns to respective antigen types, on the basis of the associated reference position and the respective associated further positions, and determine respective measures of binding, wherein the respective measures of binding indicate respective bindings of antibodies of the biological sample to respective antigen types, on the basis of the second image information item.

16. The device as claimed in claim 15,
further comprising:
at least one illumination unit for emitting excitation light for exciting an emission of first fluorescence radiation of a first wavelength range due to the first dye.

17. A data network device for automated image processing for detection of antibodies in a liquid biological sample, comprising:
at least one data interface configured to
receive at least one first image information item, wherein the at least one first image information item represents a color of the reference spots and of the antigen spots of the antigen chip as claimed in claim 1 due to a first dye, and
receive a second image information item, wherein the second information item represents a potential color of the antigen spots of the antigen chip as claimed in claim 1 due to a second dye, after incubation of the reference spots and the antigen spots of the antigen chip with the biological sample and with a conjugate, wherein the conjugate comprises a secondary antibody labeled with the second dye,
and
at least one computing unit configured to
detect the reference pattern and an associated reference position, on the basis of the at least one first image information item,
detect the respective antigen spot patterns and respective associated further positions, on the basis of the at least one first image information item,
generate an assignment information item, wherein the assignment information item indicates an assignment of the respective antigen spot patterns to respective antigen types, on the basis of the associated reference position and the respective associated further positions, and
to determine respective measures of binding, wherein the respective measures of binding indicate respective bindings of antibodies of the biological sample to respective antigen types, on the basis of the second image information item.

18. A computer readable medium having commands stored thereon, the commands being executable to cause a computer to carry out the method as claimed in claim 9.

19. A slide comprising a multiplicity of the antigen chip as claimed in claim 1.

20. A kit for detection of antibodies in a sample, comprising:
at least one of the antigen chip as claimed in claim 1, and
a conjugate, wherein the conjugate comprises a secondary antibody labeled with a second dye.

21. The kit as claimed in claim 20, wherein the second dye is selected from the group consisting of a fluorescent dye, a chromogenic substrate, and an enzyme or a substrate for a chemiluminescence reaction.

* * * * *

UNITED STATES PATENT AND TRADEMARK OFFICE
CERTIFICATE OF CORRECTION

PATENT NO. : 11,305,289 B2
APPLICATION NO. : 17/250216
DATED : April 19, 2022
INVENTOR(S) : Katja Morgenroth et al.

Page 1 of 1

It is certified that error appears in the above-identified patent and that said Letters Patent is hereby corrected as shown below:

On the Title Page

Item (30) under Foreign Application Priority Data, the foreign priority currently reads:
"July 6, 2018　(EP) ... 8182266"
And should read:
--July 6, 2018　(EP) ...18182266--.

On the second page Item (56) under Foreign Patent Documents, one of the references currently reads:
"JP 201350719　　　3/2013"
And should read:
--JP 2013508719　　　03/2013--.

On the second page Item (56) under Other Publications, one of the references currently reads:
"Extended European Search Report dated Jul. 23, 2019 in European Application No.1917943.3..."
And should read:
--Extended European Search Report dated Jul. 23, 2019 in European Application number 19179434.6--.

On the second page Item (56) under Other Publications, one of the references currently reads:
"Japanese Office Action dated Oct. 12, 2021in Japanese Application No. 2021-500209, with English translation, 9 pages."
And should read:
--Japanese Office Action dated Oct. 12, 2021 in Japanese Application No. 2021-500209, with English translation, 9 pages.--.

Signed and Sealed this
Fourteenth Day of June, 2022

Katherine Kelly Vidal
*Director of the United States Patent and Trademark Office*